United States Patent [19]
Lundquist et al.

[11] Patent Number: 6,013,863
[45] Date of Patent: Jan. 11, 2000

[54] FERTILE TRANSGENIC CORN PLANTS

[75] Inventors: Ronald C. Lundquist, Minnetonka; David A. Walters, Bloomington, both of Minn.

[73] Assignee: Dekalb Genetics Corporation, Dekalb, Ill.

[21] Appl. No.: 08/844,555

[22] Filed: Apr. 21, 1997

Related U.S. Application Data

[62] Division of application No. 08/677,695, Jul. 10, 1996, which is a continuation of application No. 07/974,379, Nov. 10, 1992, Pat. No. 5,538,877, which is a continuation of application No. 07/467,983, Jan. 22, 1990, abandoned.

[51] Int. Cl.⁷ .......................... C12N 15/00; C12N 15/82; A01H 1/06; A01H 4/00
[52] U.S. Cl. .......................... 800/293; 800/278; 800/288; 800/300; 435/430; 435/285.3
[58] Field of Search ................................. 800/205, 200, 800/250, DIG. 56, 293, 278, 288; 47/58, DIG. 1; 435/172.3, 172.1, 412, 424, 430, 430.1, 287, 285, 285.3

[56] References Cited

U.S. PATENT DOCUMENTS

| | | | |
|---|---|---|---|
| 4,370,160 | 1/1983 | Ziemelis | 71/117 |
| 4,399,216 | 8/1983 | Axel et al. | 435/6 |
| 4,520,113 | 5/1985 | Gallo et al. | 436/504 |
| 4,535,060 | 8/1985 | Comai | 435/172.3 |
| 4,536,475 | 8/1985 | Anderson | 435/172.3 |
| 4,559,301 | 12/1985 | Turner | 435/76 |
| 4,559,302 | 12/1985 | Ingolia | 435/172.3 |
| 4,581,847 | 4/1986 | Hibberd et al. | 47/58 |
| 4,634,665 | 1/1987 | Axel et al. | 435/68 |
| 4,642,411 | 2/1987 | Hibberd et al. | 800/1 |
| 4,665,030 | 5/1987 | Close | 435/240 |
| 4,666,844 | 5/1987 | Cheng | 435/240 |
| 4,683,202 | 7/1987 | Mullis | 435/91 |
| 4,708,818 | 11/1987 | Montagnier et al. | 435/5 |
| 4,727,028 | 2/1988 | Santerre et al. | 435/240.2 |
| 4,743,548 | 5/1988 | Crossway et al. | 435/172.3 |
| 4,761,373 | 8/1988 | Anderson et al. | 435/172.3 |
| 4,806,483 | 2/1989 | Wang | 435/240.49 |
| 4,885,357 | 12/1989 | Larkins et al. | 530/373 |
| 4,886,878 | 12/1989 | Larkins et al. | 536/26 |
| 4,940,835 | 7/1990 | Shah et al. | 800/205 |
| 4,945,050 | 7/1990 | Sanford et al. | 435/172.1 |
| 4,956,282 | 9/1990 | Goodman et al. | 435/69.51 |
| 4,971,908 | 11/1990 | Kishore et al. | 435/172.1 |
| 5,001,060 | 3/1991 | Peacock et al. | 435/172.3 |
| 5,004,863 | 4/1991 | Umbeck | 800/205 |
| 5,013,658 | 5/1991 | Dooner et al. | 435/172.3 |
| 5,015,580 | 5/1991 | Christou et al. | 435/172.3 |
| 5,034,322 | 7/1991 | Rogers et al. | 435/172.3 |
| 5,036,006 | 7/1991 | Sanford et al. | 435/170.1 |
| 5,049,500 | 9/1991 | Arnizen et al. | 435/172.3 |
| 5,077,399 | 12/1991 | Brauer et al. | 536/27 |
| 5,082,767 | 1/1992 | Hatfield et al. | 435/6 |
| 5,094,945 | 3/1992 | Comai | 435/172.3 |
| 5,110,732 | 5/1992 | Benfey et al. | 435/172.3 |
| 5,134,074 | 7/1992 | Gordon et al. | 435/240.4 |

(List continued on next page.)

FOREIGN PATENT DOCUMENTS

| | | | |
|---|---|---|---|
| B-80893/87 | 12/1988 | Australia | C12N 15/00 |
| 2032443 A1 | 12/1990 | Canada | C12N 15/87 |
| 0 126 537 A2 | 4/1983 | European Pat. Off. | |
| 0 131 623 B1 | 1/1984 | European Pat. Off. | C12N 15/11 |
| 0 141 373 A3 | 5/1985 | European Pat. Off. | A01G 7/00 |
| 0 142 924 A2 | 5/1985 | European Pat. Off. | C12N 15/00 |
| 0 154 204 A2 | 9/1985 | European Pat. Off. | C12N 15/00 |
| 0 160 390 A2 | 11/1985 | European Pat. Off. | A01H 15/10 |
| 0 174 791 A2 | 3/1986 | European Pat. Off. | C12N 15/00 |
| 0 189 707 A2 | 8/1986 | European Pat. Off. | C12N 15/00 |
| 0 193 259 A1 | 9/1986 | European Pat. Off. | C12N 15/00 |
| 0 204 549 A2 | 10/1986 | European Pat. Off. | C12N 15/00 |
| 0 202 668 A2 | 11/1986 | European Pat. Off. | C12N 5/02 |
| 0 242 236 A1 | 10/1987 | European Pat. Off. | C12N 15/00 |
| 0 242 246 A1 | 10/1987 | European Pat. Off. | C12N 15/00 |
| 0 299 552 A1 | 1/1988 | European Pat. Off. | C12N 15/00 |
| 0 257 472 A2 | 3/1988 | European Pat. Off. | C12N 15/00 |
| 0 262 971 A2 | 5/1988 | European Pat. Off. | A01H 1/02 |
| 0 269 601 A2 | 6/1988 | European Pat. Off. | C12N 15/00 |
| 0 270 356 A2 | 6/1988 | European Pat. Off. | C12N 15/00 |
| 0 271 408 A2 | 6/1988 | European Pat. Off. | C12N 15/00 |
| 0 275 069 A2 | 7/1988 | European Pat. Off. | C12N 15/00 |

(List continued on next page.)

OTHER PUBLICATIONS

U.S. application No. 07/392,176, Adams et al., Aug. 9, 1989.
U.S. application Ser. No. 07/205,155, Entitled "Stable Transformation of Plant Cells", pp. 1–29, Filed Jun. 10, 1988.
"'Bullets' Transform Plant Cells", *Agricell Report,* 9 (Jul. 1987).
Catalog, Handbook of Fine Chemicals, Aldrich Chem. Co., p. 508 (1988).
"Cornell U. Gene Gun Hits Biotech Bullseye", *Agriculture Technology,* p. 13.
"Dalapon", Merck Index, 11th Edition, Budavae, S., (ed.), Merck and Co., pp. 405–406 (1989).
Dialog Search of Japanese Patent No. 61–134343 (1986).
EPO Notice Regarding Publication of Bibliographic Data for EPO 0485506 (1992).
"Herbicide–Resistant Corn", *CT Academy of Science and Engineering, Case Reports,* 5, 6 (1990).
International Search Report, PCT/US 90/04462, mailed Jan. 15, 1991.
International Search Report, PCT/US 94/09699, mailed Aug. 16, 1995.
Office Action dated May 30, 1989, Goldman et al., USSN 06/880,271, filed Jun. 30, 1986.
Office Action dated Mar. 8, 1990, Goldman et al., USSN 06/880,271, filed Jun. 30, 1986.
Patent Family Record for Australian Patent 8780893.

(List continued on next page.)

*Primary Examiner*—Gary Benzion
*Attorney, Agent, or Firm*—Schwegman, Lundberg, Woessner & Kluth, P.A.

[57] ABSTRACT

A process of preparing fertile *Zea mays* plants is provided wherein said plants are resistant to the herbicide glyphosate, as well as processes for preparing seed, human food or animal feed therefrom.

8 Claims, 6 Drawing Sheets

U.S. PATENT DOCUMENTS

| | | |
|---|---|---|
| 5,145,777 | 9/1992 | Goodman et al. ................. 435/172.3 |
| 5,164,310 | 11/1992 | Smith et al. ........................ 435/172.3 |
| 5,177,010 | 1/1993 | Goldman et al. .................. 435/172.3 |
| 5,187,073 | 2/1993 | Goldman et al. .................. 435/172.3 |
| 5,188,642 | 2/1993 | Shah et al. ................................ 47/58 |
| 5,188,958 | 2/1993 | Moloney et al. ................... 435/240.4 |
| 5,196,342 | 3/1993 | Donovan ............................. 435/320.1 |
| 5,215,912 | 6/1993 | Hoffman ............................. 435/240.4 |
| 5,240,841 | 8/1993 | Johnston et al. ................... 435/172.3 |
| 5,250,515 | 10/1993 | Fuchs et al. .............................. 514/12 |
| 5,254,799 | 10/1993 | DeGreve et al. ....................... 800/205 |
| 5,258,300 | 11/1993 | Glassman et al. ................. 435/240.4 |
| 5,268,463 | 12/1993 | Jefferson ............................... 536/23.7 |
| 5,273,894 | 12/1993 | Strauch et al. .......................... 435/129 |
| 5,276,268 | 1/1994 | Strauch et al. ......................... 800/205 |
| 5,278,325 | 1/1994 | Strop et al. .............................. 554/12 |
| 5,290,924 | 3/1994 | Last et al. .............................. 536/24.1 |
| 5,310,667 | 5/1994 | Eichholtz et al. .................. 435/172.3 |
| 5,350,689 | 9/1994 | Shillito et al. .................... 435/240.47 |
| 5,352,605 | 10/1994 | Fraley et al. ......................... 435/240.4 |
| 5,371,003 | 12/1994 | Murry et al. ........................ 435/172.3 |
| 5,371,015 | 12/1994 | Sanford et al. ........................ 435/287 |
| 5,380,831 | 1/1995 | Adang et al. ........................ 536/23.71 |
| 5,436,393 | 7/1995 | Rocha-Sosa et al. ................. 800/205 |
| 5,464,763 | 11/1995 | Schilperoort et al. ............. 435/172.3 |
| 5,484,956 | 1/1996 | Lundquist et al. ..................... 800/205 |
| 5,489,520 | 2/1996 | Adams et al. ....................... 435/172.3 |
| 5,495,071 | 2/1996 | Fischhoff et al. ...................... 800/205 |
| 5,500,365 | 3/1996 | Fischhhoff et al. ................. 435/240.4 |
| 5,508,468 | 4/1996 | Lundquist et al. ..................... 800/205 |
| 5,538,877 | 7/1996 | Lundquist et al. .................. 435/172.3 |
| 5,538,880 | 7/1996 | Lundquist et al. .................. 435/172.3 |
| 5,550,318 | 8/1996 | Adams et al. ........................... 800/205 |
| 5,554,798 | 9/1996 | Lundquist et al. ..................... 800/205 |
| 5,561,236 | 10/1996 | Leemans et al. ....................... 800/205 |
| 5,565,347 | 10/1996 | Fillatti et al. ........................ 435/172.3 |
| 5,567,600 | 10/1996 | Adang et al. ......................... 536/23.71 |
| 5,567,862 | 10/1996 | Adang et al. ........................... 800/205 |
| 5,576,203 | 11/1996 | Hoffman ............................. 435/172.3 |
| 5,578,702 | 11/1996 | Adang et al. ........................... 530/350 |
| 5,580,716 | 12/1996 | Johnston et al. ............................ 435/5 |
| 5,589,616 | 12/1996 | Hoffman et al. ....................... 800/205 |
| 5,595,733 | 1/1997 | Carswell et al. ..................... 424/93.21 |
| 5,596,131 | 1/1997 | Horn et al. .............................. 800/205 |
| 5,623,067 | 4/1997 | Vanderkerckhove et al. ......... 536/24.1 |
| 5,641,876 | 6/1997 | McElroy et al. ....................... 536/24.1 |
| 5,693,507 | 12/1997 | Daniell et al. ....................... 435/172.3 |
| 5,780,708 | 7/1998 | Lundquist et al. ..................... 800/205 |
| 5,886,244 | 3/1999 | Tomes et al. ............................ 800/293 |
| 7,392,176 | 8/1989 | Adams et al. . |

FOREIGN PATENT DOCUMENTS

| | | |
|---|---|---|
| 0 280 400 A2 | 8/1988 | European Pat. Off. .......... A01C 1/06 |
| 0 282 164 A2 | 9/1988 | European Pat. Off. ........... C12N 5/00 |
| 0 289 479 A2 | 11/1988 | European Pat. Off. ......... C12N 15/00 |
| 0 290 395 A2 | 11/1988 | European Pat. Off. ......... C12N 15/00 |
| 0 292 435 A1 | 11/1988 | European Pat. Off. ......... C12N 15/00 |
| 0 301 749 A2 | 2/1989 | European Pat. Off. ......... C12N 15/00 |
| 0 331 083 A2 | 9/1989 | European Pat. Off. ......... C12N 15/00 |
| 0 331 855 A2 | 9/1989 | European Pat. Off. ......... C12M 3/00 |
| 0 334 539 A2 | 9/1989 | European Pat. Off. ......... C12N 15/00 |
| 0 335 528 A2 | 10/1989 | European Pat. Off. ......... C12N 15/00 |
| 0 348 348 A2 | 12/1989 | European Pat. Off. ....... A01N 65/00 |
| 0 442 174 A1 | 4/1991 | European Pat. Off. ......... C12N 15/82 |
| 3 738 874 A1 | 11/1988 | Germany ......................... A01H 1/06 |
| 61-134343 | 5/1984 | Japan . |
| 8 801 444 | 1/1990 | Netherlands ................... C12N 15/87 |
| 2 159 173 | 11/1985 | United Kingdom . |
| 85/01856 | 5/1985 | WIPO ............................ A01B 76/00 |
| 85/02972 | 7/1985 | WIPO ............................. A01C 1/06 |
| 86/01536 | 3/1986 | WIPO ............................. C12P 15/00 |
| 86/03776 | 7/1986 | WIPO ............................ C12N 15/00 |
| 87/04181 | 7/1987 | WIPO .............................. C12N 1/00 |
| 87/05629 | 9/1987 | WIPO ............................ C12N 15/00 |
| 88/08034 | 10/1988 | WIPO ............................ C12P 21/00 |
| 89/04371 | 5/1989 | WIPO ............................ C12N 21/00 |
| 89/10396 | 11/1989 | WIPO .............................. C12N 5/00 |
| 89/11789 | 12/1989 | WIPO .............................. A01H 1/00 |
| 89/12102 | 12/1989 | WIPO ............................ C12N 15/00 |

OTHER PUBLICATIONS

"Shotgunning DNA into Cells", *Genetic Engineering News*, (Jul./Aug. 1987).

Adang, M.J., et al., "Characterized Full–Length and Truncated Plasmid Clones of the Crystal Protein of *Bacillus thuringiensis* subsp. *kurstaki* HD–73 and Their Toxicity to *Manduca sexta*", *Gene*, 36, 289–300 (1985).

Ahokas, H., "Electrophoretic Transfection of Cereal Grains with Exogenous Nucleic Acid", Soc. Biochem. Biophys. Microbio. Fen., Biotieteen Paivat (Bioscience Days), Abstracts, Technical University of Helsinki, Espoo, p. 2 (1989).

Ahokas, H., "Transfection of Germinating Barley Seed Electrophoretically with Exogenous DNA", *Theor. Appl. Genet.*, 77, 469–472 (1989).

Altenbach, S.B., et al., "Cloning and Sequence Analysis of a cDNA Encoding a Brazil Nut Protein Exceptionally Rich in Methionine", *Plant Mol. Biol.*, 8, 239–250 (1987).

Altenbach, S.B., et al., "Enhancement of the Methionine Content of Seed Proteins by the Expression of a Chimeric Gene Encoding a Methionine–Rich Protein in Transgenic Plants", *Plant. Mol. Biol.*, 13, 513–522 (1989).

Ampe, C., et al., "The Amino–Acid Sequence of the 25 Sulphur–Rich from Seed of Brazil Nut (*Bertholletia excelsa* H.B.K.)", *Eur. J. Biochem.*, 159, 597–604 (1986).

Armstrong, C.L., et al., "Genetic and Cytogenetic Variation in Plants Regenerated from Organogenic and Friable, Embryonic Tissue Cultures of Maize", *Biol. Abstracts*, 85, Abstract 117662 (1988).

Armstrong, C.L., et al., "Establishment and Maintenance of Friable, Embryogenic Maize Callus and the Involvement of L–Proline", *Planta*, 164, 207–214 (1985).

Barker, R.F., et al., "Nucleotide Sequence of the T–DNA Region from the *Agrobacterium tumefaciens* Octopone Ti Plasmid pTil5955", *Plant Mol. Biol.*, 2, 335–350 (1983).

Benner, M.S., et al., "Genetic Analysis of Methionine–Rich Storage Protein Accumulation in Maize", *Theor. Appl. Genet.*, 78, 761–767 (1989).

Bevan, M., et al., "A Chimaeric Antibiotic Resistance Gene as a Selectable Marker for Plant Cell Transformation", *Nature*, 304, 184–187 (1983).

Bevan, M., et al., "Structure and Transcription of the Nopaline Synthase Gene Region of T–DNA", *Nuc. Acids Res.*, 11, 369–385 (1983).

Binns, A.N., "Agrobacterium–Mediated Gene Delivery and the Biology of Host Range Limitations", *Physiol. Plant.*, 79, 135–139 (1990).

Booy, G., et al., "Attempted Pollen–Mediated Transformation of Maize", *J. Plant Physiol.*, 135, 319–324 (1989).

Botterman, J., et al., "Engineering Herbicide Resistance in Plants," *Trends in Genetics*, 4, 221–222 (Aug. 1988).

Boulton, M.I., et al., "Specificity of Agrobacterium–Mediated Delivery of Maize Streak Virus DNA to Members of the Gramineae", *Plant Mol. Biol.*, 12, 31–40 (1989).

Boyer, J.S., "Water Deficits and Photosynthesis", In: *Water Deficits and Plant Growth*, vol. IV, Kozlowski, T.T., (ed.), Academic Press, New York, 153–190 (1976).

Brill, W.J., "Agricultural Microbiology", *Scientific American*, 245, 199–215 (Sep., 1981).

Buchanan–Wollaston, V., et al., "Detoxification of the Herbicide Dalapon by Transformed Plants", *J. Cell. Biochem.*, 13D, 330, Abstract No. M503 (1989).

Callis, J., et al., "Introns Increase Gene Expression in Cultured Maize Cells", *Genes and Development*, 1, 1183–1200 (1987).

Cao, J., et al., "Transformation of Rice and Maize Using the Biolistic Process", In: *Plant Gene Transfer*, Lamb, C.J., et al., (eds.), Alan R. Liss, Inc., New York, 21–33, (1990).

Carpita, N.C., "The Biochemistry of "Growing" Cells Walls", In: *Physiology of Cell Expansion During Plant Growth*, Cosgrove, D.J., et al., (eds.), Am. Soc. Plant Physiologists, 28–100 (1987).

Chandler, V.L., et al., "Two Regulatory Genes of the Maize Anthocyanin Pathway are Homologous: Isolation of B Utilizing R Genomic Sequences", *The Plant Cell*, 1, 1175–1183 (1989).

Charest, P.J., et al., "Factors Affecting the Use of Chloramphenicol Acetyltransferase as a Marker for Brassica Genetic Transformation", *Plant Cell Reports*, 7, 628–631 (1989).

Chourey, P.S., et al., "Callus Formation from Protoplasts of a Maize Cell Culture", *Theor. Appl. Genet.*, 59, 341–344 (1981).

Christou, P., et al., "Cotransformation Frequencies of Foreign Genes in Soybean Cell Cultures", *Theor. Appl. Genet.*, 79, 337–341 (1990).

Christou, P., et al., "Opine Synthesis in Wild–Type Plant Tissue", *Plant Physiol.*, 82, 218–221 (1986).

Christou, P., et al., "Soybean Genetic Engineering—Commercial Production of Transgenic Plants", *Trends in Biotechnol.*, 8, 145–151 (1990).

Christou, P., et al., "Stable Transformation of Soybean Callus by DNA–Coated Gold Particles," *Plant Physiol.*, 87, 671–674 (1988).

Chu, C.–C., et al., "Establishment of an Efficient Medium for Anther Culture of Rice through Comparative Experiments on the Nitrogen Sources", *Sci. Sin. (Peking)*, 13, 659–668 (1975).

Cocking, F., et al., "Gene Transfer in Cereals", *Science*, 236, 1259–1262 (1987).

Coe, E.H., et al., "The Genetics of Corn", In: *Corn and Corn Improvement*, 2nd Edition, Sprague, G.F., (ed.), Am. Soc. Agronomy, Inc., Madison, WI, p. 138 (1977).

Comai, L., et al., "Expression in Plants of a Mutant aroA Gene from *Salmonella typhimurium* Confers Tolerance to Glyphosate", *Nature*, 317, 741–744 (Oct. 1985).

Creissen, G., et al., "Agrobacterium– and Microprojectile–Mediated Viral DNA Delivery into Barely Microspore–Derived Cultures", *Plant Cell Rep.*, 8, 680–683 (Apr. 1990).

Crossway, A., et al., "Integration of Foreign DNA Following Microinjection of Tobacco Mesophyll Protoplasts", *Mol. Gen. Genet.*, 202, 179–185 (1986).

Darvill, A., et al., "The Primary Cell Walls of Flowering Plants", In: *The Biochemistry of Plants*, vol. 1, Academic Press, Inc., New York, 91–162 (1980).

Dauce–Lereverand, B., et al., "Improvement of *Escherichia coli* Strains Overproducing Lysine Using Recombinant DNA Techniques", *Euro. J. Appl. Microbiol. and Biotechnol.*, 15, 227–231 (1982).

De Block, M., et al., "Engineering Herbicide Resistance on Plants by Expression of a Detoxifying Enzyme", *EMBO J.*, 6, 2513–2518 (1987).

De Greef, W., et al., "Evaluation of Herbicide Resistance in Transgenic Crops under Field Conditions", *Bio/Technol.*, 7, 61–64 (1989).

Dekeyser, R.A., et al., "Evaluation of Selectable Markers for Rice Transformation", *Plant Physiol.*, 90, 217–223 (1989).

Dekeyser, R.A., et al., "Transient Gene Expression in Intact and Organized Rice Tissues", *The Plant Cell*, 2, 591–602 (1990).

Dewald, S.G., et al., "Plant Regeneration from Inbred Maize Suspensions", VIIth Intl. Cong. on Plant Tissue and Cell Culture, p. 12, Abstract No. A1–36 (Jun. 24–29, 1990).

Dewet, J.M.J., et al., "Exogenous Gene transfer in Maize (*Zea mays*) Using DNA–Treated Pollen", In: *The Experimental Manipulation of Ovule Tissues*, Chapman, G.P., et al., (eds.), Longman, New York, 197–209 (1985).

Dewet, J.R., et al., "Cloning of Firefly Luciferase cDNA and the Expression of Active Luciferase in *Escherichia coli*", *Proc. Natl. Acad. Sci. USA*, 82, 7870–7873 (1985).

Evans, D.A., et al., "Somaclonal Variation—Genetic Basis and Breeding Applications", *Trends in Genet.*, 5, 46–50 (1989).

Fransz, P., et al., "Cytodifferentiation During Callus Initiation and Somatic Embryogenesis in *Zea mays* L.", Ph.D. Thesis, Univ. of Wageningen Press, The Netherlands (1988).

Freeling, J.C., et al., "Development Potentials of Maize Tissue Cultures", *Maydica*, XXI, 97–112 (Jul. 1977).

Freiberg, B., "More Researchers Discover Corn Transformation Technology", *AG Biotechnology News*, p. 26 (1990).

Fromm, M., et al., "Expression of Genes Transfected into Monocot and Dicot Plant Cells by Electroporation", *Proc. Nat. Acad. Sci. USA*, 82, 5824–5828 (1985).

Fromm, M.E., et al., "Stable Transformation of Maize after Gene Transfer by Electroporation", *Nature*, 319, 791–793 (1986).

Fry, S.C., "Introduction to the Growing Cell Wall", In: *The Growing Plant Cell Wall: Chemical and Metabolic Analysis*, Longman Scientific and Technical, New York, pp. 1–5, 102–109 (1988).

Geiser, M., et al., "The Hypervariable Region on the Genes Coding for Entomopathogenic Crystal Proteins of *Bacillus thuringiensis:* Nucleotide Sequence of the kurhd1 gene of subsp. kurstaki HD1", *Gene*, 48, 109–118 (1986).

Goff, S.A., et al., "Plant Regeneration of Anthocyanin Biosynthetic Genes Following Transfer of B Regulatory Genes into Maize Tissues", *EMOB J.*, 9, 2517–2522 (1990).

Gordon–Kamm, W.J., et al., "Stable Transformation of Embryonic Maize Cultures by Microprojectile Bombardment", *J. Cell. Biochem.*, 13D, p. 259, Abstract No. M122 (1989).

Gould, O., et al., "Shoot Tip Culture as a Potential Transformation System", Abstracts, Beltwide Cotton Production Research Conferences, New Orleans, LA, p. 91 (1988).

Graves, A., et al., "The transformation of *Zea mays* seedlings with *Agrobacterium tumefaciens*", *Plant Mol. Biol.*, 7, 43–50 (1986).

Green, C., et al., "Plant Regeneration in Tissue Cultures of Maize", In: *Maize for Biological Research*, Sheridan, W.F., (ed.), Plant Mol. Biol. Assoc., pp. 367–372 (1982).

Green, C., et al., "Plant Regeneration from Tissue Cultures of Maize", *Crop Sci.*, 15, 417–421 (1975).

Green, C., et al., "Somatic Cell Genetic Systems in Corn", In: *Advances in Gene Technology: Molecular Genetics of Plants and Animals,* Academic Press, Inc., New York, pp. 147–157 (1983).

Grimsley, N., et al., "DNA Transfer from Agrobacterium to *Zea mays* or Brassica by Agroinfection is Dependent on Bacterial Virulence Functions", *Mol. Gen. Genet.,* 217, 309–316 (1989).

Gritz, L., et al., "Plasmid–Encoded Hygromycin B Resistance: The Sequence of Hygromycin B Phosphotransferase Gene and Its Expression in *Escherichia coli* and *Saccharomyces cerevisiae*", *Gene,* 25, 179–188 (1983).

Guerineau, F., et al., "Sulfonamide Resistance gene for Plant Transformation", *Plant Mol. Biol.,* 15, 127–136 (1990).

Guilley, H., et al., "Transcription of Cauliflower Mosaic Virus DNA: Detection of Promoter Sequences, and Characterization of Transcripts", *Cell,* 30, 763–773 (Oct. 1982).

Hallauer, A.R., et al., "Corn Breeding", In: *Corn and Corn Improvement,* 3rd Edition, Sprague, G.F., et al., (eds.), Agronomy Soc. Am., pp. 463–564 (1988).

Haughn, G.W., "Transformation with a Mutant Arabidopsis Acetolactate Synthase Gene Renders Tobacco Resistant to Sulfonylurea Herbicides", *Mol. Gen. Genet.,* 211, 266–271 (1988).

Hauptmann, R.M., et al., "Evaluation of Selectable Markers for Obtaining Stable Tranformants on the Gramineae", *Plant Physiol.,* 86, 602–606 (1988).

Herrera–Estrella, L., et al., "Use of Reporter Genes to Study Gene Expression in Plant Cells", In: *Plant Molecular Biology Manual B1,* Kluwer Academic Publishers, Dordrecht, pp. 1–22 (1988).

Hoffman, L.M., et al., "A Modified Storage Protein is Synthesized, Processed, and Degraded in the Seeds of Transgenic Plants", *Plant Mol. Biol.,* 11, 717–729 (1988).

Hoffman, L.M., et al., "Synthesis and Protein Body Deposition of Maize 15kD Zein in Transgenic Tobacco Seeds", *EMBO J.,* 6, 3213–3221 (1987).

Hofte, H., et al., "Insecticidal Crystal Proteins of *Bacillus thuringiensis*", *Microbiol. Rev.,* 53, 242–255 (1989).

Hooykaas, P.J., et al., "Transformation of Plant Cell via Agrobacterium", *Plant Mol. Biol.,* 13, 327–336 (1989).

Hooykaas–Van Slogteren, G.M.S., et al., "Expression of Ti Plasmid Genes in Monocotyledonous Plants Infected with *Agrobacterium tumefaciens*", *Nature,* 311, 763–764 (Oct. 25, 1984).

Horn, M., et al., "Transgenic Plants of Orchard Grass (*Dactylis glomerata* L.). from Protoplasts", *Chem. Abstracts,* 110, Abstract No. 89869a, 208 (1989).

Horn, M., et al., "Transgenic Plants of Orchardgrass (*Dactylis glomerata* L.) from Protoplasts", *Plant Cell Reports,* 7, 469 (1988).

Huang, Y., et al., "Factors Influencing Stable Transformations of Maize Protoplasts by Electroporation", *Plant Cell, Tissue and Organ Culture,* 18, 281 (1989).

Imbrie–Milligan, C., et al., "Microcallus Growth from Maize Protoplasts", *Planta,* 171, 58–64 (1987).

Jefferson, R., "Assayig Chimeric Genes in Plants: the GUS Gene Fusion System", *Plant Mol. Biol. Rep.,* 5, 387–405 (1987).

Jefferson, R., et al., "β–Glucuronidase from *Escherichia coli* as a Gene–Fusion Marker", *Proc. Nat. Acad. Sci. USA,* 83, 8447–8451 (1986).

Jefferson, R., et al., "GUS Fusions: β–Glucuronidase as a Sensitive and Versatile Gene Fusion Marker in Higher Plants", *EMBO J.,* 6, 3901–3907 (1987).

Johri, M.M., et al., "Genetic Approaches to Meristem Organization", In: *Maize for Biological Research,* Sheridan, W.F., (ed.), Plant Mol. Biol. Assoc., pp. 301–310 (1982).

Jones, H., et al., "Recent Advances in Plant Electroporation", *Oxford Surveys of Plant Mol. and Cell Biol.,* 4, 347–357 (1987).

Jones, H., et al., "Transient Gene Expression in Electroporated Solanum Protoplasts", *Plant Mol. Biol.,* 13, 503–511 (1989).

Kaeppler, H.F., et al., "Silicon Carbide Fiber–Mediated DNA Delivery into Plant Cells", *Plant Cell Rep.,* 9, 415–418 (1990).

Kamo, K., et al., "Establishment and Characterization of Long–Term Embryonic Maize Callus and Cell Suspension Cultures", *Plant Sci.,* 45, 111–117 (1986).

Kamo, K., et al., "Regeneration of *Zea mays* L. from Embryogenic Callus", *Bot. Gaz.,* 146, 327–334 (1985).

Kao, K.N., et al., "Nutritional Requirements for Growth of *Vicia hajastana* Cells and Protoplasts at a Very Low Population Density in Liquid Media", *Planta,* 126, 105–110 (1978).

Kartha, K., et al., "Transient Expression of Chloramphenicol Acetyl Transferase (CAT) Gene in Barley Cell Cultures and Immature Embryos Through Microprojectile Bombardment", *Plant Cell. Rep.,* 8, 429–432 (1989).

Kay, R., et al., "Duplication of CaMV 35S Promoter Sequences Creates a Strong Enhancer for Plant Genes", *Science,* 236, 1299–1302 (Jun. 5, 1987).

Kirihara, J., et al., "Differential Expression of a Gene for a Methionine–Rich Storage Protein in Maize", *Mol. Gen. Genet.,* 211, 477–484 (1988).

Kirihara, J., et al., "Isolation and Sequence of a Gene Encoding a Methionine–Rich 10–kD Zein Protein from Maize", *Gene,* 71, 359–370 (1988).

Klein, T., et al., "Genetic Transformation of Maize Cells by Particle Bombardment", *Plant Physiol.,* 91, 440–444 (1989).

Klein, T., et al., "Regulation of Anthocyanin Biosynthetic Genes Introduced into Intact Maize Tissue by Microprojectiles", *Proc. Nat. Acad. Sci. USA,* 86, 6682–6685 (1989).

Klein, T., et al., "Genetic Transformation of Maize Cells by Particle Bombardment and the Influence of Methylation on Foreign Gene Expression", In: *Gene Manipulation in Plant Improvement II,* Gustafson, J.P., (ed.), Plenum Press, New York, 265–266 (1990).

Klein, T., et al., "Transfer of Foreign Genes into Intact Maize Cells with High–Velocity Microprojectiles", *Proc. Nat. Acad. Sci. USA,* 85, 4305–4309 (1988).

Klein, T.M., et al., "Factors Influencing Gene Delivery into *Zea mays* Cells by High Velocity Microprojectiles", *Bio/Technol.,* 6, 559–563 (1988).

Klein, T.M., et al., "High Velocity Microprojectiles for Delivering Nucleic Acids to Living Cells", *Nature,* 327, 70–73 (1987).

Kozac, M., "Complication and Analysis of Sequence from the Translation Start Site in Eukaryotic mRNAs", *Nuc. Acids Res.,* 12, 857–871 (1984).

Kozac, M., "Point Mutations Define a Sequence Flanking the AUG Initiator Codon that Modulates Translation by Eukaryotic Ribosomes", *Cell,* 44, 283–292 (1986).

Kuhlemeier, C., et al., "Regulation of Gene Expression in Higher Plants", *Ann. Rev. Plant Physiol.,* 38, 234–239 (1987).

Lazzeri, P., et al., "In Vitro Genetic Manipulation of Cereals and Grasses", *Ad. Cell Culture,* 6, 291–293 (1988).

Lee, J.S., et al., "Gene Transfer into Intact Cells of Tobacco by Electroporation", *Korean J. Genet.,* 11, 65–72 (1989).

Levitt, J., "Growth Regulators", In: *Introduction to Plant Physiology,* The C.V. Mosby Company, St. Louis, p. 241 (1969).

Lindsey, K., et al., "Electroporation of Cells", *Physiol. Plant.,* 79, 168–172 (1990).

Lindsey, K., et al., "Stable Transformation of Sugarbeet Protoplasts by Electroporation", *Plant Cell Rep.,* 8, 71–74 (1989).

Lindsey, K., et al., "The Permeability of Electroporated Cells and Protoplasts of Sugar Beet", *Planta,* 172, 346–355 (1987).

Lindsey, K., et al., "Transient Gene Expression in Electroporated Protoplasts and Intact Cells of Sugar Beet", *Plant Mol. Biol.,* 10, 43–52 (1987).

Lorz, H., et al., "Advances in Tissue Cultures and Progress Towards Genetic Transformation of Cereals", *Plant Breeding,* 100, 1–25 (1988).

Lu, C., et al., "Improved Efficiency of Somatic Embryogenesis and Plant Regeneration on Tissue Cultures of Maize(*Zea mays* L.)", *Theor. Appl. Genet.,* 66, 285–289 (1983).

Lu, C., et al., "Somatic Embryogenesis in *Zea mays* L.", *Theor. Appl. Genet,* 62, 109–112 (1982).

Ludwig, S., et al., "A Regulatory Gene as a Novel Visible Marker for Maize Transformation", *Science,* 247, 449–450 (1990).

Ludwig, S., et al., "High Frequency Callus Formation from Maize Protoplasts", *Theor. Appl. Genet.,* 71, 344–350 (1985).

Ludwig, S., et al., "Lc, a Member of the Maize R Gene Family Responsible for Tissue–Specific Anthocyanin Production, Encodes a Protein Similar to Transcriptional Activators and Contains the myc–Homology Region", *Proc. Nat. Acad. Sci. USA,* 86, 7092–7096 (1989).

Ludwig, S., et al., "Maize R Gene Family: Tissue–Specific Helix–Loop–Helix Proteins", *Cell,* 62, 849–851 (1990).

Lutcke, H., et al., "Selection of AUG Initiation Codons Differs in Plants and Animals", *EMBO J.,* 6, 43–48 (1987).

Mariani, C., et al., "Engineered Male Sterility in Plants", *Symposia of the Society for Experimental Biology,* Number XLV, Proceedings of a Meeting Held at the University of Glasgow, Scotland, 271–279 (1991).

Masumura, T., et al., "cDNA Cloning of an mRNA Encoding a Sulfur–Rich 10 kDa Prolamin Polypeptide in Rice Seeds", *Plant Mol. Biol.,* 12, 123–130 (1989).

McCabe, D.E., et al., "Stable Transformation of Soybean (*Glycine max*) by Particle Acceleration", *Bio/Technol.,* 6, 923–926 (1988).

McDaniel, C., et al., "Cell–Lineage Patterns in the Shoot Apical Meristem of the Germinating Maize Embryo", *Planta,* 175, 13–22 (1988).

Meadows, M., "Characterization of Cells and Protoplasts of the B73 Maize Cell Line", *Plant Sci. Lett.,* 28, 337–348 (1982/83).

Mendel, R., et al., "Delivery of Foreign Genes to Intact Barley Cell by High–Velocity Microprojectiles", *Theor. Appl. Genet.,* 78, 31–34 (1989).

Messing, J., "Corn Storage Protein: A Molecular Genetic Model", Division of Energy BioSciences—Summaries of FY 1990 Activities, p. 70, Abstract No. 135 (1990).

Milborrow, B.V., "Abscisic Acid and Other Hormones", In: *The Physiology and Biochemistry of Drought Resistance in Plants,* Paleg, L.G., et al., (eds.), Academic Press, Inc., New York, pp. 347–388 (1981).

Morikawa, H., et al., "Gene Transfer into Intact Plant Cells by Electroporation through Cell Walls and Membranes", *Gene,* 41, 121 (1986).

Morocz, S., et al., "An Improved System to Obtain Fertile Regenerants via Maize Protoplasts Isolated from a Highly Embryonic Suspension Culture", *Theor. Appl. Genet.,* 80, 721–726 (1990).

Morocz, S., et al., "Two Approaches to Rendering *Zea mays* L. Applicable to Tissue Culture Manipulations", Abstracts, VIIth Intl. Cong. on Plant Tissue and Cell Culture, Amsterdam, A1–102, Abstract No. 209, p. 190 (1990).

Murakami, T., et al., "The Bialaphos Biosynthetic Genes of *Streptomyces hygroscopicus:* Molecular Cloning and Characterization of the Gene Cluster", *Mol. Gen. Genet.,* 205, 42–50 (1986).

Murashige, T., et al., "A Revised Medium for Rapid Growth and Bio Assays with Tobacco Tissue Cultures", *Physiol. Plant.,* 15, 473–497 (1962).

Murphy, H.L., "New Dekalb–Pfizer Seed Chief to Harvest R & D Breakthroughs", *Crain's Business Weekly,* pp. 38–39 (1990).

Murray, E.E., et al., "Codon Usage in Plant Genes", *Nuc. Acids Res.,* 17, 477–498 (1989).

Nelson, R.S., "Virus Tolerance, Plant Growth, and Field Performance of Transgenic Tomato Plants Expressing Coat Protein from Tobacco Mosaic Virus", *Bio/Technol.,* 6, 403–409 (1988).

Nelson, T., "New Horses for Monocot Gene Jockeys", *The Plant Cell,* 2, 589 (Jul., 1990).

Neuffer, M.G., "Growing Maize for Genetic Purposes", Maize for Biological Research, Plant Mol. Biol. Assoc., pp. 19–30 (1988).

Odell, J., et al., "Identification of DNA Sequences Required for Activity of the Cauliflower Mosaic Virus 35S Promoter", *Nature,* 313, 810–811 (1985).

Ohta, Y., et al., "High–Efficiency Genetic Transformation of Maize by a Mixture of Pollen and Exogenous DNA", *Pro. Nat. Acad. Sci. USA,* 83, 715–719 (1986).

Okta, Y., et al., "Gene Manifestation of Exogenous DNA Applied to Self–Propagating Stigma (Gene Action Revealed in the M1 and M2 Generations from Self–Pollination Applying Exogenous DNA", *Jap. J. Breed.,* 30, 184–185 (1980).

Ozias–Akins, P., et al., "In vitro Regeneration and Genetic Manipulation of Grasses", *Physiol. Plant.,* 73, 565–569 (1988).

Ozias–Akins, P., et al., "Progress and Limitations in the Culture of Cereal Protoplasts", *Trends in Biotechnol.,* 2, 119–123 (1984).

Parker, W.B., et al., "Selection and Characterization of Sethoxydim–Tolerant Maize Tissue Cultures", *Plant Physiol.,* 92, 1220–1225 (1990).

Pederson, K., et al., "Sequence Analysis and Characterization of a Maize Gene Encoding a High–Sulfur Zein Protein of $M_1$ 15,000", *J. Biol. Chem.,* 261, 6279–6284 (1986).

Phillips, R.L., et al., "Cell/Tissue Culture and In Vitro Manipulation", In: *Corn and Corn Improvement,* 3rd Edition, Sprague, G.F., et al., (eds.), Agronomy Soc. Am., pp. 345–387 (1988).

Phillips, R.L., et al., "Elevated Protein–Bound Methionine in Seeds of a Maize Line Resistant to Lysine Plus Threonine", *Cereal Chem.,* 62, 213–218 (1985).

Poehlman, J., "Breeding Corn (Maize)", In: *Breeding Field Crops,* 3rd Edition, AVI Publishing Co., Westport, CT, pp. 452, 469–471, 477–481 (1986).

Potrykus, I., "Gene Transfer to Cereals: An Assessment" *Bio/Technol.,* 8, 535–542 (Jun. 1990).

Potrykus, I., "Gene Transfer to Cereals: An Assessment", *Trends Biotechnol.,* 7, 269–273 (Oct. 1989).

Potrykus, I., "Gene Transfer to Plants: Assessment and Perspectives", *Physiol. Plant.,* 79, 125–134 (1990).

Potrykus, I., et al., "Callus Formation from Cell Culture Protoplasts of Corn (*Zea mays* L.)", *Theor. Appl. Genet.* 54, 209–214 (1979).

Potrykus, I., et al., "Callus Formation from Stem Protoplasts of Corn (*Zea mays* L.)", *Mol. Gen. Genet.,* 156, 347–350 (1977).

Potter, H. et al., "Enhancer–Dependent Expression of Human κ Immunoglobulin Genes Introduced into Mouse Pre–B Lymphocytes by Electroporation", *Pro. Nat. Acad. Sci. USA,* 81, 7161–7165 (1984).

Prioli, L.M., et al., "Plant Regeneration and Recovery of Fertile Plants from Protoplasts of Maize (*Zea mays* L.)", *Bio/Technol.,* 7, 589–594 (Jun. 1989).

Puite, K.J., et al., "Electrofusion, a Simple and Reproducible Technique in Somatic Hybridization of *Nicotiana plumbaginifolia* Mutants", *Plant Cell Rep.,* 4, 274–276 (1985).

Ranch, J.P., et al., "Expression of 5–Methyltryptophan Resistance in Plants Regenerated from Resistant Cell Lines of *Datura innoxia*", *Plant Physiol.,* 71, 136–140 (1983).

Rhodes, C.A., "Corn: from Protoplasts to Fertile Plants", *Bio/Technol.,* 7, 548 (Jun. 1989).

Rhodes, C.A., "Genetically Transformed Maize Plants from Protoplasts", *Science,* 240, 204–207 (Apr. 8, 1988).

Rhodes, C.A., et al., "Plant Regeneration from Protoplasts Isolated from Embryogenic Maize Cell Cultures", *Bio/Technol.,* 6, 56–60 (Jan. 1988).

Richaud, F., et al., "Chromosomal Location and Nucleotide Sequence of the *Escherichia coli* dapA Gene", *Biol. Abstracts,* 82, p. AB–391, Abstract No. 3396 (1986).

Richaud, F., et al., "Chromosomal Location and Nucleotide Sequence of the *Escherichia coli* dapA Gene", *J. Bacteriol.,* 166, 297–300 (1986).

Robertson, D.S., "Loss of Mu Mutator Activity When Active Mu Systems are Transferred to Inbred Lines", *Maize Genetics Coop. Newsletter,* 60, 10 (1986).

Ross, M.C., et al., "Transient and Stable Transgenic Cells and Calli of Tobacco and Maize Following Microprojectile Bombardment", *J. Cell. Biochem.,* 13D, p. 268, Abstract No. M149 (1989).

Sahi, S.V., et al., "Metabolites in Maize Which Affect Virulence Induction in *Agrobacterium tumefaciens*", *Plant Physiol., Supplement,* p. 86, Abstract No. 514 (1989).

Sanford, J.C., "Biolistic Plant Transformation", *Physiol. Plant.,* 79, 206–209 (1990).

Sanford, J.C., "The Biolistic Process", *Trends Biotechnol.,* 6, 299–302 (1988).

Sanford, J.C., et al., "Attempted Pollen–Mediated Plant Transformation Employing Genomic Donor DNA", *Theor. Appl. Genet.,* 69, 571–574 (1985).

Sanford, J.C., et al., "Delivery of Substances into Cells and Tissues Using a Particle Bombardment Process", *Particulate Sci. Technol.,* 5, 27–37 (1987).

Sass, J.E., "Morphology: Development of the Caryopsis", In: *Corn and Corn Improvement,* 2nd Edition, Sprauge, G.F., (ed.), Am. Soc. Agronomy, pp. 89, 98 (1977).

Schmidt, A., et al., "Media and Environmental Effects of Phenolics Production from Tobacco Cell Cultures", *Chem. Abstracts.,* 110, p. 514, Abstract No. 230156z (1989).

Shigekawa, K., et al., "Electroporation of Eukaryotes and Prokaryotes: A General Approach to the Introduction of Macromolecules into Cells", *BioTechniques,* 6, 742–751 (1988).

Shillito, R.D., et al., "High Efficiency Direct Gene Transfer to Plants", *Bio/Technol.,* 3, 1099 (1985).

Shillito, R.D., et al., "Regeneration of Fertile Plants from Protoplasts of Elite Inbred Maize", *Bio/Technol.,* 7, 581–587 (Jun. 1989).

Shimamoto, K., et al., "Fertile Transgenic Rice Plants Regenerated from Transformed Protoplasts", *Nature,* 338, 274–278 (1989).

Shotwell, M.A., et al., "The Biochemistry of Plants—A Comprehensive Treatise", In: *The Biochemistry of Plants,* vol. 15, Marcus, A., (ed.), Academic Press, Inc., San Diego, pp. 297–345 (1989).

Smith, R., et al., "Shoot Apex Explant for Transformation", *Plant Physiol.* (*Suppl.*), 86, p. 108, Abstract 646 (1988).

Soberon, X., et al., "Construction and Characterization of New Cloning Vehicles, IV. Deletion Derivatives of pBR322 and pBR325", *Gene,* 9, 287–305 (1980).

Spencer, T.M., et al., "Bialaphos Selection of Stable Transformations from Maize Cell Culture", *Theor. Appl. Genet.,* 79, 625–631 (May 1990).

Spencer, T.M., et al., "Fertile Transgenic Maize", Abstracts, 7th Annual Meeting, Mid–Atlantic Plant Mol. Biol. Soc., p. 30 (1990).

Spencer, T.M., et al., "Segregation of Transgenes in Maize", *Plant Mol. Biol.* 18, 201–210 (1992).

Spencer, T.M., et al., "Selection of Stable Transformants from Maize Suspension Cultures Using the Herbicide Bialaphos", Poster Presentation, FASEB Plant Gene Expression Conference, Copper Mountain, Colorado (Aug. 8, 1989).

Sprague, G.F., et al., "Corn Breeding", In: *Corn and Corn Improvement,* Sprague, G. F., (ed.), Am. Soc. Agronomy, Inc., Madison, WI, pp. 305, 320–323 (1977).

Sugiyama, M., et al., "Use of the Tyrosinase Gene from Streptomyces to Probe Promoter Sequences for *Escherichia coli*", *Plasmid,* 23, 237–241 (1990).

Thompson, C., et al., "Characterization of the Herbicide–Resistance Gene bar from *Streptomyces hygroscopicus*", *EMBO J.,* 6, 2519–2523 (1987).

Tomes, D.T., et al., "Transgenic Tobacco Plants and Their Progeny Derived by Microprojectile Bombardment of Tobacco Leaves", *Plant Mol. Biol.,* 14, 261–268 (Feb. 1990).

Twell, D., et al., "Transient Expression of Chimeric Genes Delivered into Pollen by Microprojectile Bombardment", *Plant Physiol.,* 91, 1271–1274 (1989).

Ulian, E., et al., "Transformation of Plants via the Shoot Apex", *In Vitro Cell. Dev. Biol.,* 9, 951–954 (1988).

Usami, S., et al., "Absence in Monocotyledonous Plants of the Diffusable Plant Factors including T–DNA Circularization and vir Gene Expression in Agrobacterium", *Mol. Gen. Genet.,* 209, 221–226 (1987).

Vasil, I.K., et al., "Culture of Protoplasts Isolated from Embryogenic Cell Suspension Cultures of Sugarcane and Maize", *IAPTC Abstracts,* p. 443 (1986).

Vasil, I.K., et al., "Isolation and Maintenance of Embryogenic Cell Suspension Cultures of Gramineae", In: *Cell Culture and Somatic Cell Genetics of Plants,* vol. I, Academic Press, Inc., pp. 152–158 (1984).

Vasil, V., et al., "Plant Regeneration from Friable Embryonic Callus and Cell Suspension Cultures of *Zea mays* L.", *J. Plant Physiol.,* 124, 399–408 (1986).

Walbot, V., et al., "Molecular Genetics of Corn", In: *Corn and Corn Improvement,* 3rd Edition, Sprague, G.F., et al., (eds.), Am. Soc. Agronomy, Madison, WI, pp. 389–430 (1988).

Waldron, C., et al., "Resistance to Hygromycin B", *Plant Mol. Biol.,* 5, 103–108 (1985).

Wang, Y., et al., "Transient Expression of Foreign Genes in Rice, Wheat and Soybean Cells Following Particle Bombardment", *Plant Mol. Biol.,* 11, 433–439 (1988).

Weising, K., et al., "Foreign Genes in Plants: Transfer, Structure, Expression and Applications", *Ann. Rev. Genet.,* 22, 421–478 (1988).

White, J., et al., "A Cassette Containing the bar Gene of *Streptomyces hygroscopicus:* a Selectable Marker for Plant Transformation", *Nuc. Acid. Res.,* 18, 1062 (1989).

Whiteley, H.R., et al., "The Molecular Biology of Parasporal Crystal Body Formation in *Bacillus thuringiensis*", *Ann. Rev. Microbiol.,* 40, 549–576 (1986).

Yang, H., et al., "Production of Kanamycin Resistant Rice Tissues Following DNA Uptake into Protoplasts", *Plant Cell Rep.,* 7, 421 (1988).

Yanisch–Perron, L., et al., "Improved M13 Phage Vectors and Host Strains: Nucleotide Sequences of the M13mp18 and pUC19 Vectors", *Gene,* 33, 103–119 (1985).

Yugari, Y., et al., "Coordinated End–Product Inhibition in Lysine Synthesis in *Escherichia coli*", *Biochem. Biophys. Acta.,* 62, 612–614 (1962).

Abe, K., et al., "Molecular Cloning of a Cysteine Proteinase Inhibitor of Rice (Oryzacystatin)", *The Journal of Biological Chemistry,* 262, 16793–16797 (Dec. 15, 1987).

Anderson, J.M., et al., "The Encoded Primary Sequence of a Rice Seed ADP–glucose Pyrophosphorylase Subunit and Its Homology to the Bacterial Enzyme", *The Journal of Biological Chemistry,* 264, 12238–12242 (Jul. 25, 1989).

Bol, J.F., et al., "Plant Pathogenesis–Related Proteins Induced by Virus Infection", *Annu. Rev. Phytopathol.,* 28, 113–138 (1990).

Depicker, A.G., et al., "A Negative Selection Scheme for Tobacco Protoplast–Derived Cells Expressing the T–DNA Gene 2", *Plant Cell Reports,* 7, 63–66 (1988).

Domoney, C., et al., "Cloning and Characterization of Complementary DNA for Convicilin, a Major Seed Storage Protein in *Pisum sativum* L.", *Planta,* 159, 446–453 (1983).

Dunn, G.M., et al., "Inheritance of Cyclic Hydroxamates in *Zea mays* L.", *Can. J. Plant Sci.,* 61, 583–593 (Jul. 1981).

Gepts, P., et al., "Enhanced Available Methionine Concentration Associated with Higher Phaseolin Levels in Common Bean Seeds", *Theor. Appl. Genet.,* 69, 47–53 (1984).

Guerrero, F.D., et al., "Turgor–Responsive Gene Transcription and RNA Levels Increase Rapidly When Pea Shoots are Wilted. Sequence and Expression of Three Inducible Genes", *Plant Mol. Biol.,* 15, 11–26 (1990).

Hu, N.T., et al., "Primary Structure of a Genomic Zein Sequence of Maize", *The EMBO Journal,* 1, 1337–1342 (1982).

Jaworski, J.G., et al., "A Cerulenin Insensitive Short Chain 3–Ketoacyl–Acyl Carrier Protein Synthase in *Spinacia oleracea* Leaves", *Plant Physiol.,* 90, 41–44 (1989).

Josefsson, L.G., et al., "Structure of a Gene Encoding the 1.7 S Storage Protein, Napin, from *Brassica napus*", *The Journal of Biological Chemistry,* 262, 12196–12201 (Sep. 5, 1987).

Kim, C.S., et al., "Improvement of Nutritional Value and Functional Properties of Soybean Glycinin by Protein Engineering", *Protein Engineering,* 3, 725–731 (1990).

Malan, C., et al., "Correlation Between CuZn Superoxide Dismutase and Glutathione Reductase, and Environmental and Xenobiotic Stress Tolerance in Maize Inbreds", *Plant Science,* 69, 157–166 (1990).

Marks, M.D., et al., "Nucleotide Sequence Analysis of Zein mRNAs from Maize Endosperm", *The Journal of Biological Chemistry,* 260, 16451–16459 (Dec. 25, 1985).

Montoliu, L., et al., "A Tandem of α–Tubulin Genes Preferentially Expressed in Radicular Tissues from *Zea mays*", *Plant Molecular Biology,* 14, 1–15 (1989).

Mundy, J., et al., "Selective Expression of a Probable Amylase/Protease Inhibitor in Barley Aleurone Cells: Comparison to the Barley Amylase/Subtilisin Inhibitor", *Planta,* 169, 51–63 (1986).

O'Reilly, D.R., et al., "A Baculovirus Blocks Insect Molting by Producing Ecdysteroid UDP–Glucosyl Transferase", *Science,* 245, 1110–1112 (Sep. 8, 1989).

Smith, I.K., et al., "Properties and Functions of Glutathione Reductase in Plants", *Physiol. Plant.,* 77, 449–456 (1989).

Stalker, D.M., et al., "Herbicide Resistance in Transgenic Plants Expressing a Bacterial Detoxification Gene", *Science,* 242, 419–242 (Oct. 21, 1988).

Viotti, A., et al., "Each Zein Gene Class Can Produce Polypeptides of Different Sizes", *The EMBO Journal,* 4, 1103–1110 (1985).

Werr, W., et al., "Structure of the Sucrose Synthase Gene on Chromosome 9 of *Zea mays* L.", *The EMBO Journal,* 4, 1373–1380 (1985).

Yenofsky, R.L., et al., "Isolation and Characterization of a Soybean (*Glycine max*) Lipoxygenase–3 Gene", *Mol. Gen. Genet.,* 211, 215–222 (1988).

Flavell, R., et al., "Prospects for Transforming Monocot Crop Plants", *Nature,* 307, 108–109 (Jan. 12, 1984).

Goodman, R.M., et al., "Gene Transfer in Crop Improvement", *Science,* 236, 48–54 (Apr. 3, 1987).

Paszkowski, J., et al., "Direct Gene Transfer to Plants", *The EMBO Journal,* 3, 2717–2722 (1984).

Potrykus, I., et al., "Direct Gene Transfer to Cells of a Graminaceous Monocot", *Mol. Gen. Genet.,* 199, 183–188 (1985).

Armstrong, C.L., et al., "Genetic and Cytogenetic Variation in Plants Regenerated from Organogenic and Friable, Embryogenic Tissue Cultures in Maize", *Crop Science,* 28, 363–369 (1988).

Dure III, L., et al., "Common Amino Acid Sequence Domains Among the LEA Proteins of Higher Plants", *Plant Molecular Biology,* 12, 475–486 (1989).

Hong, B., et al., "Cloning and Characterization of cDNA Encoding a mRNA Rapidly–Induced by ABA in Barley Aleurone Layers", *Plant Molecular Biology,* 11, 495–506 (1988).

Mundy, J., et al., "Abscisic Acid and Water–Stress Induce the Expression of a Novel Rice Gene", *The EMBO Journal,* 7, 2279–2286 (1988).

Andrews, D.L., et al., "Characterization of the Lipid Acyl Hydrolase Activity of the Major Potato (*Solanum tuberosum*) Tuber Protein, Patatin, by Cloning and Abundant Expression in a Baculovirus Vector", *Biochem. J.,* 252, 199–206 (1988).

Fromm, M.E., et al., "Inheritance and Expression of Chimeric Genes in the Progeny of Transgenic Maize Plants", *Bio/Technology,* 8, 833–839 (1990).

Jaynes, J.M., et al., "Plant Protein Improvement by Genetic Engineering: Use of Synthetic Genes", *Trends in Biotechnology*, 4, 314–320 (Dec. 1986).

Poehlman, J.M., "Backcross Breeding", In: *Breeding Field Crops, 3rd Edition*, AVI Publishing Company, Inc., Westport, CT, 203–206 (1988).

*In Vitro Cellular & Developmental Biology*, 21, Program Issue: Thirty–Sixth Annual Meeting of the Tissue Culture Association, New Orleans, LA, 88 p. (Mar. 1985).

*In Vitro Cellular & Developmental Biology*, 23, Program Issue: Thirty–Eighth Annual Meeting of the Tissue Culture Association, Washington, D.C., 93 p. (Mar. 1987).

*In Vitro Cellular & Developmental Biology*, 24, Program Issue: Thirty–Ninth Annual Meeting of the Tissue Culture Association, Las Vegas, NV, 92 p. (Mar. 1988).

*In Vitro Cellular & Developmental Biology*, 25, Program Issue: Fortieth Annual Meeting of the Tissue Culture Association, Orlando, FL, 73 p. (Mar. 1989).

"European Firm Devises Insect–Resistant Plants", *Agricultural Biotechnology News*, 1, 6 (Mar.–Apr. 1986).

"Molecular Strategies for Crop Improvement", *Journal of Cellular Biochemistry*, Supplement 14e, List of Plenary and Poster Sessions, organized by Arntzen, C., et al., for The Keystone Conference on Molecular Strategies for Crop Plant Improvement, held at the 19th UCLA Symposia, 257 (1990).

Abbe, E.C., et al., "The Growth of the Shoot Apex in Maize: Embryogeny", *American Journal of Botany*, 41, 285–293 (Apr. 1954).

Adang, M.J., et al., "Expression of a *Bacillus thuringiensis* Insecticidal Crystal Protein Gene in Tobacco Plants", *Molecular Strategies for Crop Protection*, Arntzen, C.J., et al. (eds.), Alan R. Liss, Inc., New York, 345–353 (1987).

Anderson, P.C., et al., "Herbicide–Tolerant Mutants of Corn", *Genome*, 31, 994–999 (1989).

Angus, T.A., "Implications of Some Recent Studies of *Bacillus thuringiensis*—A Personal Purview", *Proceedings of the 4th International Colloquium on Insect Pathology*, College Park, MD, 183–189 (Aug. 25–28, 1970).

Armaleo, D., et al. "Biolistic Nuclear Transformation of *Saccharomyces cerevisiae* and Other Fungi", *Curr. Genet.*, 17, 97–103 (1990).

Aronson, A.I., et al., "*Bacillus thuringiensis* and Related Insect Pathogens", *Microbiological Reviews*, 50, 1–24 (Mar. 1986).

Aronson, J.N., et al., "Toxic Trypsin Digest Fragment from the *Bacillus thuringiensis* Parasporal Protein", *Applied and Environmental Microbiology*, 53, 416–421 (Feb. 1987).

Barton, K.A., et al., "*Bacillus thuringiensis* δ–Endotoxin Expressed in Transgenic *Nicotiana tabacum* Provides Resistance to Lepidopteran Insects", *Plant Physiol.*, 85, 1103–1109 (1987).

Birk, Y., et al., "Separation of a Tribolium–Protease Inhibitor from Soybeans on a Calcium Phosphate Column", *Biochem. Biophys. Acta*, 67, 326–328 (Feb. 12, 1963).

Bishop, D.H., et al., "Genetically Engineered Viral Insecticides—A Progress Report 1986–1989", *Pestic. Sci.*, 27, 173–189 (1989).

Boynton, J.E., et al., "Chloroplast Transformation in Chlamydomonas with High Velocity Microprojectiles", *Science*, 240, 1534–1537 (Jun. 10, 1988).

Bryant, J.A., "At Last: Transgenic Cereal Plants from Genetically Engineered Protoplasts", *Trends in Biotechnology*, 6, 291–292 (Dec. 1988).

Burgerjon, A., et al., "Industrial and International Standardization of Microbial Pesticides—I. *Bacillus thuringiensis*", *Entomophaga*, 22, 121–129 (1977).

Busvine, J.R., *A Critical Review of the Techniques for Testing Insecticides*, Table of Contents, Commonwealth Agricultural Bureaux, Slough, England, iii–xi (1971).

Bytebier, B., et al., "T–DNA Organization in Tumor Cultures and Transgenic Plants of the Monocotyledon *Asparagus officinalis*", *Proc. Natl. Acad. Sci. USA*, 84, 5345–5349 (Aug. 1987).

Calabrese, D.M., et al., "A Comparison of Protein Crystal Subunit Sizes in *Bacillus thuringiensis*", *Canadian Journal of Microbiology*, 26, 1006–1010 (Aug. 1980).

Caplan, A., et al., "Introduction of Genetic Material into Plant Cells", *Science*, 222, 815–821 (Nov. 18, 1983).

Chaleff, R.S., "Induction, Maintenance, and Differentiation of Rice Callus Cultures on Ammonium as Sole Nitrogen Source", *Plant Cell Tissue Organ Culture*, 2, 29–37 (1983).

Christou, P., et al., "Inheritance and Expression of Foreign Genes in Transgenic Soybean Plants", *Proc. Natl. Acad. Sci. USA*, 86, 7500–7504 (Oct. 1989).

Cooksey, K.E., "Purification of a Protein from *Bacillus thuringiensis* Toxic to Larvae of Lepidoptera", *Biochem. J.*, 106, 445–454 (1968).

De Block, M., et al., "Expression of Foreign Genes in Regenerated Plants and Their Progeny", *EMBO J.*, 3, 1681–1689 (1984).

De Block, M., et al., "The Use of Phosphinothricin Resistance as a Selectable Marker in Tobacco Protoplast Transformation", In: *Progress in Plant Protoplast Research*, Proceedings of the 7th International Protoplast Symposium, Wageningen, The Netherlands, Puite, K.J., et al., (eds.), Kluwer Academic Publishers, Dordrecht, 389–390 (Dec. 6–11, 1987).

Denecke, J., et al., "Quantification of Transient Expression Levels of Genes Transferred to Plant Protoplasts by Electroporation", *Progress in Plant Protoplast Research*, Puite, K.J., et al., (eds.), Proceedings of the 7th International Protoplast Symposium, Wageningen, The Netherlands, 337–338 (Dec. 6–11, 1987).

Duncan, D.R., et al., "The Production of Callus Capable of Plant Regeneration for Immature Embryos of Numerous *Zea Mays* Genotypes", *Planta*, 165, 322–332 (1985).

Dunleavy, J.M., "*Curtobacterium plantarum* sp. nov. Is Ubiquitous in Plant Leaves and Is Seed Transmitted in Soybean and Corn", *International Journal of Systematic Bacteriology*, 39, 240–249 (Jul. 1989).

Dybvig, K., et al., "Transposition of Gram–Positive Transposon Tn916 in *Acholeplasma laidlawii* and *Mycoplasma pulmonis*", *Science*, 235, 1392–1394 (Mar. 13, 1987).

Edallo, S., et al., "Chromosomal Variation and Frequency of Spontaneous Mutation Associated with in vitro Culture and Plant Regeneration in Maize", *Maydica*, 26, 39–56 (1981).

Fast, P.G., et al., "*Bacillus thuringiensis* δ–Endotoxin: Evidence that Toxin Acts at the Surface of Susceptible Cells", *Experientia*, 34, 762–763 (1978).

Faust, R.M., et al., "Bacteria and Their Toxins as Insecticides", In: *Microbial and Viral Pesticides*, Kurstak, E., (ed.), Marcel Dekker, Inc., New York, 75–208 (1982).

Finkle, B.J., et al., "Growth and Regeneration of Alfalfa Callus Lines After Freezing in Liquid Nitrogen", *Plant Science*, 42, 133–140 (1985).

Finney, D.J., In: *Probit Analysis: A Statistical Treatment of the Sigmoid Response Curve*, iii–ix (1952).

Fischhoff, D.A., et al., "Insect Tolerant Transgenic Tomato Plants", *Bio/technology*, 5, 807–812 (1987).

Fukuto, T.R., "Physicochemical Aspects of Insecticidal Action", In: *Insecticidal Biochemistry and Physiology*, Wilkinson, C.F., (ed.), Plenum Press, New York, 397–428 (1976).

Gallagher, S., "Progress and Promise of the Particle Gun", *Ag Biotechnology News*, 6, 12–13 (Mar.–Apr. 1989).

Gallie, D.R., et al., "The 5'–leader Sequence of Tobacco Mosaic Virus RNA Enhances the Expression of Foreign Gene Transcripts in Vitro and in Vivo", *Nucleic Acids Research*, 15, 3257–3273 (1987).

Gatehouse, A.M.R., et al., "Assessment of the Antimetabolic Effects of Trypsin Inhibitors from Cowpea (*Vigna unguiculata*) and Other Legumes on Development of the Bruchid Beetle *Callosobruchus maculatus*", *J. Sci. Food Agric.*, 34, 345–350 (1983).

Genovesi, A.D., et al., "Embryogenesis in Callus Derived from Rice Microspores", *Plant Cell Reports*, 1, 257–260 (1982).

Georghiou, G.P., et al., "Factors Influencing the Evolution of Resistance", In: *Pesticide Resistance: Strategies and Tactics for Management*, Committee on Strategies for the Management of Pesticide Resistant Pest Populations, Board on Agriculture, National Research Council, National Academy Press, Washington, D.C., 157–169 (1986).

Gerlach, W.L., "Genetic Engineering: Its Place in Plant Breeding", In: *Plant Breeding and Genetic Engineering*, Zakri, A.H., (ed.), Society for the Advancement of Breeding Researches in Asia and Oceania, Bangi, Malaysia, 269–277 (1988).

Goldfarb, B., et al., "Transient Expression of Microprojectile–Introduced DNA in Douglas–Fir", *J. Cell. Biochem.*, 13D, Abstract No. M121, p. 259 (1989).

Goldman, S.L., et al., "Transformation of *Zea mays* by *Agrobacterium tumefaciens*: Evidence for Stable Genetic Alterations", *Journal of Cellular Biochemistry*, 11B, Abstract No. F 202, p. 26 (1987).

Gordon, P.N., et al., "Plant Regeneration from Tissue Cultures of Maize", *Maize Genetics Cooperation Newsletter*, 51, 79–80 (Mar. 1, 1977).

Green, C.E., "New Development in Plant Tissue Culture and Plant Regeneration", In: *Basic Biology of New Developments in Biotechnology*, Hollaender, A., et al., (eds.), Plenum Press, New York, 195–209 (1983).

Green, C.E., "Somatic Embryogenesis and Plant Regeneration from the Friable Callus of *Zea mays*", *Proceedings of the 5th International Congress on Plant Tissue & Cell Culture*, Tokyo, Japan, 107–108 (1982).

Haccius, B., "Question of Unicellular Origin of Non–Zygotic Embryos in Callus Cultures", *Phytomorphology*, 28, 74–81 (1978).

Harms, C.T., et al., "Regeneration of Plantlets from Callus Cultures of *Zea mays* L.", *Z. Ptlanzenzuchtg. 77*, 347–351 (1976).

Hartree, E.F., "Determination of Protein: A Modification of the Lowry Method that Gives a Linear Photometric Response", *Analytical Biochemistry*, 48, 422–427 (1972).

Harvey, W.R., et al., "Potassium Ion Transport ATPase in Insect Epithelia", *J. Exp. Biol.*, 106, 91–117 (1983).

Heimpel, A.M., et al., "Recent Advances in the Knowledge of Some Bacterial Pathogens of Insects", *Proceedings of the Tenth International Congress of Entomology*, vol. 4, 711–722 (1956).

Heimpel, A.M., et al., "The Site of Action of Crystalliferous Bacteria in Lepidoptera Larvae", *Journal of Insect Pathology*, 1, 152–170 (1959).

Hernalsteens, J.–P., et al., "An Agrobacterium–Transformed Cell Culture from the Monocot *Asparagus Officinalis*", *The EMBO Journal*, 3, 3039–3041 (Dec. 1984).

Hibberd, K.A., "Induction, Selection, and Characterization of Mutants in Maize Cell Cultures", In: *Cell Culture and Somatic Cell Genetics of Plants*, vol. 1, Vasil, I.K., (ed.), Academic Press, Inc., Orlando, FL, 571–576 (1984).

Hickle, L.A., et al., "Analytical Chemistry of *Bacillus thuringiensis*: An Overview", In: *Analytical Chemistry of Bacillus thuringiensis*, Hickle, L.A., et al., (eds.), Developed from a Symposium Sponsored by the Division of Agrochemicals at the 198th National Meeting of the American Chemical Society, Miami Beach, FL, vii–ix, 1–8 (Sep. 10–15, 1989).

Hilder, V.A., et al., "A Novel Mechanism of Insect Resistance Engineered into Tobacco", *Nature*, 330, 160–163 (Nov. 12, 1987).

Hodges, T.K., et al., "Genotype Specificity of Somatic Embryogenesis and Regeneration in Maize", *Bio/technology*, 4, 219–223 (Mar. 1986).

Hodges, T.K., et al., "Regeneration of Maize", In: *Biotechnology in Plant Science*, Zaitlin, M., et al., (ed.), Academic Press, Inc., Orlando, FL, 15–33 (1985).

Hoekema, A., et al., "Codon Replacement in the PGK1 Gene of *Saccharomyces cerevisiae*: Experimental Approach to Study the Role of Biased Codon Usage in Gene Expression", *Molecular and Cellular Biology*, 7, 2914–2924 (Aug. 1987).

Hofmann, C., et al., "Binding of the Delta Endotoxin from *Bacillus thuringiensis* to Brush–Border Membrane Vesicles of the Cabbage Butterfly (*Pieris Brassicae*)", *Eur. J. Biochem.*, 173, 85–91 (1988).

Hofmann, C., et al., "Specificity of *Bacillus thuringiensis* δ–Endotoxins is Correlated with the Presence of High–Affinity Binding Sites in the Brush Border Membrane of Target Insect Midguts", *Proc. Natl. Acad. Sci. USA*, 85, 7844–7848 (Nov. 1988).

Höfte, H., et al., "Monoclonal Antibody Analysis and Insecticidal Spectrum of Three Types of Lepidopteran–Specific Insecticidal Crystal Proteins of *Bacillus thuringiensis*", *Applied and Environmental Microbiology*, 54, 2010–2017 (Aug. 1988).

Höfte, H., et al., "Structual and Functional Analysis of a Cloned Delta Endotoxin of *Bacillus thuringiensis berliner* 1715", *Eur. J. Biochem.*, 161, 273–280 (1986).

Hollingworth, R.M., "The Biochemical and Physiological Basis of Selective Toxicity", In: *Insecticidal Biochemistry and Physiology*, Wilkinson, C.F., (ed.), Plenum Press, New York, 431–506 (1976).

Horsch, R.B., et al., "A Simple and General Method for Transferring Genes into Plants", *Science*, 227, 1229–1231 (Mar. 8, 1985).

Huber, H.E., et al., "*Bacillus thuringiensis* δ–Endotoxin: Composition and Activation", In: *Pathogenesis of Invertebrate Microbial Diseases*, Davidson, E.W., (ed.), Allanheld, Osmun & Co. Publishers, Inc., Totowa, NJ, 209–234 (1981).

Huber–Lukac, M., et al., "Characterization of Monoclonal Antibodies to a Crystal Protein of *Bacillus thuringiensis* subsp. *kurstaki*", *Infection and Immunity*, 54, 228–232 (Oct. 1986).

Imbrie–Milligan, C.W., et al., "Microcallus Formation from Maize Protoplasts Prepared from Embryogenic Callus", *Planta*, 168, 395–401 (1986).

Jarrett, P., "Potency Factors in the delta–Endotoxin of *Bacillus thuringiensis* var. *aizawi* and the Significance of Plasmids in their Control", *Journal of Applied Bacteriology*, 58, 437–448 (1985).

Johnson, D.E., "Toxicity of *Bacillus thuringiensis* Entomocidal Protein Toward Cultured Insect Tissue", *Journal of Invertebrate Pathology*, 38, 94–101 (1981).

King, P., et al., "Maize", In: *Handbook of Plant Cell Culture*, vol. 2, Sharp, W.R., et al., (eds.), Macmillan Publishing Company, New York, 69–91 (1984).

Klein, T.M., et al., "Advances in Direct Gene Transfer into Cereals", In: *Genetic Engineering: Principles and Methods*, vol. 11, Setlow, J.K., (ed.), Plenum Publishing Corp., New York, 13–31 (1989).

Klein, T.M., et al., "Particle Gun Technology: A Novel Method for the Introduction of DNA into Living Cells", *Program and Abstracts for an International Symposium: "Biotechnology in Plant Science: Relevance to Agriculture in the Eighties"*, Poster, #28, Ithaca, NY, 25 (Jun. 23–27, 1985).

Klein, T.M., et al., "Stable Genetic Transformation of Intact Nicotiana Cells by the Particle Bombardment Process", *Proc. Natl. Acad. Sci. USA*, 95, 5502–5505 (Nov. 1988).

Knowles, B.H., et al., "Characterization and Partial Purification of a Plasma Membrane Receptor for *Bacillus thuringiensis* var. *Kurstaki* Lepidopteran–Specific δ–Endotoxin", *J. Cell Sci.*, 83, 89–101 (1986).

Knowles, B.H., et al., "Lectin–Like Binding of *Bacillus thuringiensis* var. *Kurstaki* Lepidopteran–Specific Toxin is an Initial Step in Insecticidal Action", *FEBS Letters*, 168, 197–202 (Mar. 1984).

Langridge, W.H., et al., "Electric Field Mediated DNA Transformation in Plant Protoplasts", *Program and Abstracts for an International Symposium: "Biotechnology in Plant Science: Relevance to Agriculture in the Eighties"*, Ithaca, NY, Poster #30, p. 25 (Jun. 23–27, 1985).

Leason, M., et al., "Inhibition of Pea Leaf Glutamine Synthetase by Methionine Sulphoximine, Phosphinothricin and Other Glutamate Analogues", *Biochemistry*, 21, 855–857 (1982).

Lee, B., "Cereal Transformation", *Plant Today*, 9–11 (Jan–Feb. 1989).

Lörz, H., et al., "Gene Transfer to Cereal Cells Mediated by Protoplast Transformation", *Mol. Gen. Genet.*, 199, 178–182 (1985).

Lowe, K., et al., "Plant Regeneration via Organogenesis and Embryogenesis in the Maize Inbred Line B73", *Plant Science*, 41, 125–132 (1985).

Luckow, V.A., et al., "Trends in the Development of Baculovirus Expression Vectors", *Bio/Technology*, 6, 47–55 (Jan. 1988).

Lüthy, P., "Insecticidal Toxins of *Bacillus thuringiensis*", *FEMS Microbiology Letters*, 8, 1–7 (1980).

Mangano, M.L., et al., "Long–Term Cold Storage of Regenerable Maize Callus", *In Vitro Cellular and Developmental Biology*, 25, Abstract No. 224, p. 66A (Mar. 1989).

Merryweather, A.T., et al., "Construction of Genetically Engineered Baculovirus Insecticides Containing the *Bacillus thuringiensis* subsp. *Kurstaki* HD–73 Delta Endotoxin", *Journal of General Virology*, 71, 1535–1544 (1990).

Molnar, S.J., et al., "Initiation of Totipotent Tissue Cultures from Undeveloped Axillary and Secondary Ears", *Maize Genetics Cooperation Newsletter*, 54, 52–53 (Mar. 31, 1980).

Murphy, D.W., et al., "*Bacillus thuringiensis* Enzyme–Digested Delta Endotoxin: Effect on Cultured Insect Cells", *Science*, 194, 954–956 (Nov. 26, 1976).

Nishiitsutsuji–Uwo, J., et al., "Mode of Action of *Bacillus thuringiensis* δ–Endotoxin: Effect on TN–368 Cells", *Journal of Invertebrate Pathology*, 34, 267–275 (1979).

Ochatt, S.J., et al., "Selection for Salt/Drought Tolerance using Isolated Protoplasts and Protoplast–Derived Calli of Colt Cherry (*Prunus avium x pseudocerasus*)", In: *Progress in Plant Protoplast Research*, Puite, K.J., et al., (eds.), Kluwer Academic Publishers, Dordrecht, The Netherlands, pp. 391–392 (1988).

Oeda, K., et al., "Formation of Crystals of the Insecticidal Proteins of *Bacillus thuringiensis* subsp. *aizawai* IPL7 in *Escherichia coli*", *Journal of Bacteriology*, 171, 3568–3571 (Jun. 1989).

Park, W.D., et al., "High–Level, Sucrose–Inducible Expression of a Chimeric Patatin–GUS Gene In Leaf Explants of Transgenic Tobacco Plants", *Journal of Cellular Biochemistry*, 13D, Abstract No. M 343, p. 310 (Mar. 27–Apr. 7, 1989).

Perlak, F.J., et al., "Expression of *Bacillus thuringiensis* Proteins in Transgenic Plants", In: *Biotechnology, Biological Pesticides and Novel Plant–Pest Resistance for Insect Pest Management*, Roberts, D.W., et al., (eds.), Insect Pathology Resource Center, Boyce Thompson Institute for Plant Research, Cornel University, Ithaca, NY, 77–81 (1988).

Poehlman, J.M., et al., In: *Breeding Field Crops*, 3rd Edition, AVI Publishing Company, Inc., Westport, CT, 149–152 (1987).

Poethig, R.S., "Maize—The Plant and Its Parts", In: *Maize for Biological Research*, Sheridan, W.F., (ed.), Plant Molecular Biology Association., Charlottesville, VA, 9–18 (1982).

Potrykus, I., et al., "Direct Gene Transfer: State of the Art and Future Potential", *Plant Molecular Biology Reporter*, 3, 117–128 (Summer 1985).

Randolph, L.F., et al., "Developmental Morphology of the Caryopsis in Maize", *Journal of Agricultural Research*, 53, 881–916 (Dec. 15, 1936).

Rhodes, C.A., et al., "Cytogenetic Stability of Aneuploid Maize Tissue Cultures", *Can. J. Genet. Cytol.*, 28, 374–384 (1986).

Rhodes, C.A., et al., "Factors Affecting Tissue Culture Initiation from Maize Tassels", *Plant Science*, 46, 225–232 (1986).

Rice, T.B., "Tissue Culture Induced Genetic Variation in Regenerated Maize Inbreds", *Proceedings of the 37th Annual Corn & Sorghum Industry Research Conference*, 148–162 (1982).

Rosahl, S., et al., "Expression of a Tuber–Specific Storage Protein In Transgenic Tobacco Plants: Demonstration Of An Esterase Activity", *EMBO. J*, 6, Press Limited, Oxford, England, 1155 (1987).

Roth, B.A., et al., "Genetic Regulation of Transient Expression of Maize Anthocyanin Pathway Genes Introduced into Intact Maize Tissues by Microprojectile Bombardment", *Journal of Cellular Biochemistry*, 13D, Abstract No. M 344, p. 310 (Mar. 27–Apr. 7, 1989).

Roush, R.T., et al., "Ecological Genetics of Insecticidal and Acaricide Resistance", *Ann. Rev. Entomol.*, 32, 361–380 (1987).

Ryan, A.J., et al., "The Expression of the Napin Gene Under the Control of Its Own Promoter in Transgenic Tobacco Plants", *Journal of Cellular Biochemistry*, 13D, Abstract No. M 345, p. 310 (Mar. 27–Apr. 7, 1989).

Sanford, J.C., "The Biolistic Process", *Plant Physiology*, 89, Abstract No. 9, p. 2 (Apr. 1989).

Sanford, J.C., "Delivery of DNA into Regenerable Tissues of Monocots, Using High–Velocity Microprojectiles", Grant Application No. 86–0183, United States Department of Agriculture, Science and Education, 57 p. (Feb. 27, 1986).

Sass, J.E., "Comparative Leaf Number in the Embryos of Some Types of Maize", *Iowa State Coll. J. Sci.*, 25, 509–512 (1951).

Schafer, W., et al., "T–DNA Integration and Expression in a Monocot Crop Plant after Induction of Agrobacterium", *Nature*, 327, 529–532 (Jun. 11, 1987).

Schardl, C.L., et al., "Design and Construction of a Versatile System for the Expression of Foreign Genes in Plants", *Gene*, 61, 1–11 (1987).

Schnepf, H.E., et al., "Delineation of a Toxin–Encoding Segment of a *Bacillus thuringiensis* Crystal Protein Gene", *The Journal of Biological Chemistry*, 260, 6273–6280 (1985).

Shaner, D.L., et al., "Mechanism of Action of the Imidazolinones and Cell Culture Selection of Tolerant Maize", In: *Biotechnology in Plant Sciences*, Zaitlin, M., et al., (eds.), Academic Press, Orlando, FL, 287–299 (1985).

Sharman, B.C., "Developmental Anatomy of the Shoot of *Zea mays* L.", *Annals of Botany*, VI, 246–281 (Apr. 1942).

Shields, R., "Towards Insect–Resistant Plants", *Nature*, 328, 12–13 (Jul. 2, 1987).

Shivakumar, A.G., et al., "Vegetative Expression of the δ–Endotoxin Genes of *Bacillus thuringiensis* subsp. *kurstaki* in *Bacillus subtilis*", *Journal of Bacteriology*, 166, 194–204 (Apr. 1986).

Smith, G.E., et al., "Molecular Engineering of the *Autographa californica* Nuclear Polyhedrosis Virus Genome: Deletion Mutations Within the Polyhedrin Gene", *Journal of Virology*, 46, 584–593 (May 1983).

St. Julian, G., et al., "Bacteria, Spirochetes, and Rickettsia as Insecticides", *Annals of the New York Academy of Sciences*, 217, 65–75 (1973).

Stolle, C.A., et al., "Cellular Factor Affecting the Stability of β–globulin mRNA", *Gene*, 62, 65–74 (1988).

Strauch, E., et al., "Cloning of a Phosphinothricin N–Acetyltransferase Gene from Streptomyces Viridochromogenes Tu494 and its Expression in *Streptomyces lividans* and *Escherichia coli*", *Gene*, 63, 65–74 (1988).

Stroo, H.F., et al., "Heterotrophic Nitrification in an Acid Forest Soil and by an Acid–Tolerant Fungus", *Applied and Environmental Microbiology*, 52, 1107–1111 (Nov. 1986).

Suprasanna, P., et al., "Plantlet Regeneration from Glume Calli of Maize (*Zea mays* L.)", *Theor. Appl. Genet.*, 72, 120–122 (1986).

Thomas, W.E., et al., "Mechanism of Action of *Bacillus thuringiensis* var *israelensis* Insecticidal δ–Endotoxin", *FEBS Letters*, 154, 362–368 (Apr. 1983).

Tojo, A., et al., "Dissolution and Degradation of *Bacillus thuringiensis* δ–Endotoxin by Gut Juice Protease of the Silkworm *Bombyx mori*", *Applied and Environmental Microbiology*, 45, 576–580 (Feb. 1983).

Tomes, D.T., "Cell Culture, Somatic Embryogenesis and Plant Regeneration in Maize, Rice, Sorghum and Millets", In: *Cereal Tissue and Cell Culture*, Bright, S.W.J., et al., (eds.), Martinus Nijnoff/Dr. W. Junk, Amsterdam, The Netherlands, 175–203 (1985).

Tomes, D.T., "Initiation of Embryogenic Callus Cultures from Immature Embryos of Elite Corn (*Zea mays* L.) Germplasm", *In Vitro*, 20, Abstract No. 146, p. 276 (Mar. 1984).

Tomes, D.T., et al., "The Effect of Parental Genotype on Initiation of Embryogenic Callus from Elite Maize (*Zea mays* L.) Germplasm", *Theor. Appl. Genet.*, 70, 505–509 (1985).

Torne, J.M., et al., "Regeneration of Plants from Mesocotyl Tissue Cultures of Immature Embryos of *Zea mays* L.", *Plant Science Letters*, 17, 339–344 (1980).

Vaeck, M., et al., "*Bacillus thuringiensis* Endotoxin Gene Expression and Insect Resistance in Higher Plants", *Pesticide Science*, 20, 319–320 (1987).

Vaeck, M., et al., "Engineering Improved Crops for Agriculture: Protection from Insects and Resistance to Herbicides", In: *Plant Gene Systems and Their Biology*, Key, J.L., et al., (eds.), Alan R. Liss, Inc., New York, 171–181 (1987).

Vaeck, M., et al., "Engineering of Insect Resistant Plants Using a *B. thuringiensis* Gene", In: *Molecular Strategies for Crop Protection*, New York, Alan R. Liss, Inc., 355–366 (1987).

Vaeck, M., et al., "Insect Resistance in Transgenic Plants Expressing *Bacillus thuringiensis* Toxin Gens", *An. Soc. Entomol. Brasil*, 16, 427–435, (1987).

Vaeck, M., et al., "Protein Engineering in Plants: Expression of *Bacillus thuringiensis* Insecticidal Protein Genes", *Cell Culture and Somatic Cell Genetics of Plants*, 6, 425–439, (1989).

Vaeck, M., et al., "Transgenic Plants Protected from Insect Attack", *Nature*, 328, 33–37, (Jul. 2, 1987).

van den Elzen, P.J., et al., "A Chimaeric Hygromycin Resistance Gene as a Selectable Marker in Plant Cells", *Plant Molecular Biology*, 5, 299–302, (1985).

van den Elzen, P.J., et al., "Simple Binary Vectors for DNA Transfer to Plant Cells", *Plant Molecular Biology*, 5, 149–154, (1985).

Van Lammeren, A.A., "Developmental Morphology and Cytology of the Young Maize Embryo (*Zea mays* L.)", *Acta Bot. Neerl.*, 35, 169–188 (Aug. 1986).

Vasil, I.K., "Isolation and Culture of Protoplasts of Grasses", *International Review of Cytology*, Supplement 16, Bourne, G.H., et al., (eds.), Academic Press, New York, 79–88 (1983).

Vasil, V., et al., "Histology of Somatic Embryogenesis in Cultured Immature Embryos of Maize (*Zea mays* L.)", *Protoplasma*, 127, 1–8 (1985).

Watson, S.A., "Corn Marketing, Processing and Utilization", In: *Corn and Corn Improvement*, 3rd Edition, Sprague, G.F., et al., (eds.), American Society of Agronomy, Inc., et al., Madison, WI, 881–939 (1988).

Weigel, Jr., R.C., et al., "Somatic Embryogenesis in Barley", *In Vitro*, 20, Abstract No. 147, p. 277 (Mar. 1984).

Weissinger, A., et al., "Maize Transformation via Microprojectile Bombardment", In: *Genetic Improvements of Agriculturally Important Crops*, Fraley, R.T., et al., (eds.), Cold Spring Harbor Laboratory, Cold Spring Harbor, NY, 21–25 (1988).

Weissinger, A., et al., "Microprojectile Bombardment for Maize Transformation", *In Vitro Cellular and Developmental Biology*, 23, Program Issue, 38th Annual Meeting of the Tissue Culture Association, Washington, D.C., Abstract No. 254 (Mar.1987).

Wernicke, W., et al., "Adventitious Embryoid and Root Formation from Rice Leaves", *Z. Pflanzenphysiol. Bd.*, 103, 361–365 (1981).

Withers, L., et al., "Proline: A Novel Cryoprotectant for the Freeze Preservation of Cultured Cells of *Zea mays* L.", *Plant Physiology*, 64, 675–678 (1979).

Witt, D.P., et al., "Cytotoxicity of *Bacillus thuringiensis* δ–Endotoxins to Cultured Cf–1 Cells Does Not Correlate with In Vivo Activity Toward Spruce Budworm Larvae", In: *Fundamental and Applied Aspects of Invertebrate Pathology*, Samson, R.A., et al., (eds.), Fourth International Colloquium of Invertebrate Pathology, Wangingen, The Netherlands, 3–6 (Aug. 18–22, 1986).

Wohlleben, W., et al., "Nucleotide Sequence of the Phosphinothricin N–Acetyltransferase Gene from *Streptomyces viridochromogenes* Tü494 and Its Expression in *Nicotania tabacum*", *Gene*, 70, 25–37 (1988).

Wood, M., "Blast Those Genes!", *Agricultural Research*, 2 p. (Jun. 1989).

PHI R₀ PLANTS

FERTILE TRANSGENIC CORN PLANTS

This application is a division of U.S. patent application Ser. No. 08/677,695, filed Jul. 10, 1996, which is a continuation of U.S. patent application Ser. No. 07/974,379, filed Nov. 10, 1992, now U.S. Pat. No. 5,538,877, which in turn is a continuation of U.S. patent application Ser. No. 07/467,983, filed Jan. 22, 1990, now abandoned.

BACKGROUND OF THE INVENTION

This invention relates to fertile transgenic plants of the species Zea mays (oftentimes referred to herein as maize or corn). The invention further relates to producing transgenic plants via particle bombardment and subsequent selection techniques which have been found to produce fertile transgenic plants.

Genetic engineering of plants, which entails the isolation and manipulation of genetic material (usually in the form of DNA or RNA) and the subsequent introduction of that genetic material into a plant or plant cells, offers considerable promise to modern agriculture and plant breeding. Increased crop food values, higher yields, feed value, reduced production costs, pest resistance, stress tolerance, drought resistance, the production of pharmaceuticals, chemicals and biological molecules as well as other beneficial traits are all potentially achievable through genetic engineering techniques. Once a gene has been identified, cloned, and engineered, it is still necessary to introduce it into a plant of interest in such a manner that the resulting plant is both fertile and capable of passing the gene on to its progeny.

A variety of methods have been developed and are currently available for the transformation of various plants and plant cells with DNA. Generally these plants have been dicotyledonous, and some success has been reported with certain of the monocotyledonous cereals. However, some species have heretofore proven untransformable by any method. Thus, previous to this discovery, no technology had been developed which would permit the production of stably transformed Zea mays plants in which the transforming DNA is heritable thereof. This failure in the art is well documented in the literature and has been discussed in a number of recent reviews (Potrykus, 1989; Weising et al., 1988; Cocking et al., 1987).

European Patent Publns. 270,356 (McCabe et al.) and 275,069 (Arntzen et al.) describe the introduction of DNA into maize pollen followed by pollination of maize ears and formation of seeds. The plants germinated from these seeds are alleged to contain the introduced DNA, but there is no suggestion that the introduced DNA was heritable, as has been accomplished in the present invention. Only if the DNA introduced into the corn is heritable can the corn be used in breeding programs as required for successful commercialization of transgenic corn.

Graves et al. (1986) claims Acrobacterium-mediated transformation of Zea mays seedlings. The alleged evidence was based upon assays known to produce incorrect results.

Despite extensive efforts to produce fertile transformed corn plants which transmit the transforming DNA to progeny, there have been no reported successes. Many previous failures have been based upon gene transfer to maize protoplasts, oftentimes derived from callus, liquid suspension culture cells, or other maize cells using a variety of transformation techniques. Although several of the techniques have resulted in successful transformation of corn cells, the resulting cells either could not be regenerated into corn plants or the corn plants produced were sterile (Rhodes et al. 1988) or, in some cases, it even turned out that the plants were in fact not transformed. Thus, while maize protoplasts and some other cells have previously been transformed, the resulting transformants could not be regenerated into fertile transgenic plants.

On the other hand, it has been known that at least certain corn callus can be regenerated to form mature plants in a rather straightforward fashion and that the resulting plants were often fertile. However, no stable transformation of maize callus was ever achieved, i.e. there were no techniques developed which would permit a successful stable transformation of a regenerable callus. An example of a maize callus transformation technique which has been tried is the use of Agrobacterium mediated transfer.

The art was thus faced with a dilemma. While it was known that corn protoplast and suspension culture cells could be transformed, no techniques were available which would regenerate the transformed protoplast into a fertile plant. While it was known that corn callus could be regenerated into a fertile plant, there were no techniques known which could transform the callus, particularly while not destroying the ability of the callus both to regenerate and to form fertile plants.

Recently, a new transformation technique has been created based upon-the bombardment of intact cells and tissues with DNA-coated microprojectiles. The technique, disclosed in Sanford et al. (1987) as well as in EPO Patent Publication 331,855 of J. C. Sanford et al. based upon U.S. Ser. No. 161,807, filed Feb. 29, 1988, has been shown effective at producing transient gene expression in some plant cells and tissues including those from onion, maize (Klein et al. 1988a), tobacco, rice, wheat, and soybean, and stable expression has been obtained in tobacco and soybeans. In fact, stable expression has been obtained by bombardment of suspension cultures of Zea mays Black Mexican Sweet (Klein et al. 1989) which cultures are, however, non-regenerable suspension culture cells, not the callus culture cells used in the process of the present invention.

No protocols have been published describing the introduction of DNA by a bombardment technique into cultures of regenerable maize cells of any type. No stable expression of a gene has been reported by means of bombardment of corn callus followed by regeneration of fertile plants and no regenerable fertile corn has resulted from DNA-coated microprojectile bombardment of the suspension cultures. Thus, the art has failed to produce fertile transformed corn plants heretofore.

A further stumbling block to the successful production of fertile transgenic maize plants has been in selecting those few transformants in such a manner that neither the regeneration capacity nor the fertility of the regenerated transformant are destroyed. Due to the generally low level of transformants produced by a transformation technique, the need for selection of the transformants is self-evident. However, selection generally entails the use of some toxic agent, e.g. herbicide or antibiotic, which can effect either the regenerability or the resultant plant fertility.

It is thus an object of the present invention to produce fertile, stably transgenic, Zea mays plants and seeds which transmit the introduced gene to progeny. It is a further object to produce such stably transgenic plants and seeds by a particle bombardment and selection process which results in a high level of viability for a few transformed cells. It is a further object to produce fertile stably transgenic plants of other graminaceous cereals besides maize.

REFERENCES CITED

Armstrong, CL, et al. (1985) J Planta 164:207–214
Callis, J, et al. (1987) Genes & Develop 1:1183–1200
Chilton & Barnes (1983) Nuc Acids Res 11:364–385
Chu, CC, et al. (1975) Sci Sin (Peking) 18:659–668
Cocking, F, et al. (1987) Science 236:1259–1262
DeWet et al. (1985) Proc Natl Sci USA 82:7870–7873
Freeling, JC, et al. (1976) Maydica XXI:97–112
Graves, A, et al. (1986) Plant Mol Biol 7:43–50
Green, C, et al. (1975) Crop Sci 15:417–421
Green, CE, (1982) Plant Tissue Culture, A Fujiwara ed. Maruzen, Tokyo, Japan pp 107–8
Green, C, et al. (1982) Maize for Biological Research, Plant Mol Biol Assoc, pp 367–372
Gritz, L, et al. (1983) Gene 25:179–188
Guilley, H, et al. (1982) Cell 30:763–773
Jefferson, R, et al. (1987) EMBO J 6:3901–3907)
Kamo, K, et al. (1985) Bot Gaz 146:327–334
Klein, T, et al. (1989) Plant Physiol 91:440–444
Klein, T, et al. (1988a) Proc Natl Acad Sci USA 85:4305–9
Klein, T, et al. (1988b) Bio/Technology 6:559–563
Lu, C, et al. (1982) Theor Appl Genet 62:109–112
McCabe, D, et al. (1988) Bio/Technology 6:923–926
Murashige, T, et al. (1962) Physiol Plant 15:473–497
Neuffer, M, (1982) Maize for Biological Research, Plant Mol Biol Assoc, pp 19–30
Phillips, R, et al. (1988) Corn and Corn Improvement, 3rd ed., Agronomy Soc Amer, pp 345–387
Potrykus, I (1989) Trends in Biotechnology 7:269–273
Rhodes, CA, et al. (1988) Science 240:204–7
Sambrook, J, et al (1989) Molecular Cloning: A Laboratory Manual, 2nd ed., Cold Spring Harbor Laboratory Press
Sanford, J, et al. (1987) J Part Sci & Techn 5:27–37
Weising, K, et al., (1988) Ann Rev of Genetics 22:421–478
Yanisch-Perron, L, et al. (1985) Gene 33:109–119

SUMMARY OF THE INVENTION

The present invention relates to fertile transgenic Zea mays plants containing heterologous DNA, preferably chromosomally integrated heterologous DNA, which is heritable by progeny thereof.

The invention further relates to all products derived from transgenic Zea mays plants, plant cells, plant parts, and seeds.

The invention further relates to transgenic Zea mays seeds stably containing heterologous DNA and progeny which inherit the heterologous DNA.

The invention further relates to a process for producing fertile transgenic Zea mays plants containing heterologous DNA. The process is based upon microprojectile bombardment, selection, and plant regeneration techniques.

The invention further relates to a process for producing fertile transformed plants of graminaceous plants other than Zea mays which have not been reliably transformed by traditional methods such as electroporation, Afrobacterium, injection, and previous ballistic techniques.

The invention further relates to regenerated fertile mature maize plants from transformed embryogenic tissue, transgenic seeds produced therefrom, and R1 and subsequent generations.

In preferred embodiments, this invention produces the fertile transgenic plants by means of a DNA-coated microprojectile bombardment of clumps of friable embryogenic callus, followed by a controlled regimen for selection of the transformed callus lines.

DESCRIPTION OF THE PREFERRED EMBODIMENTS

Figure 1A:
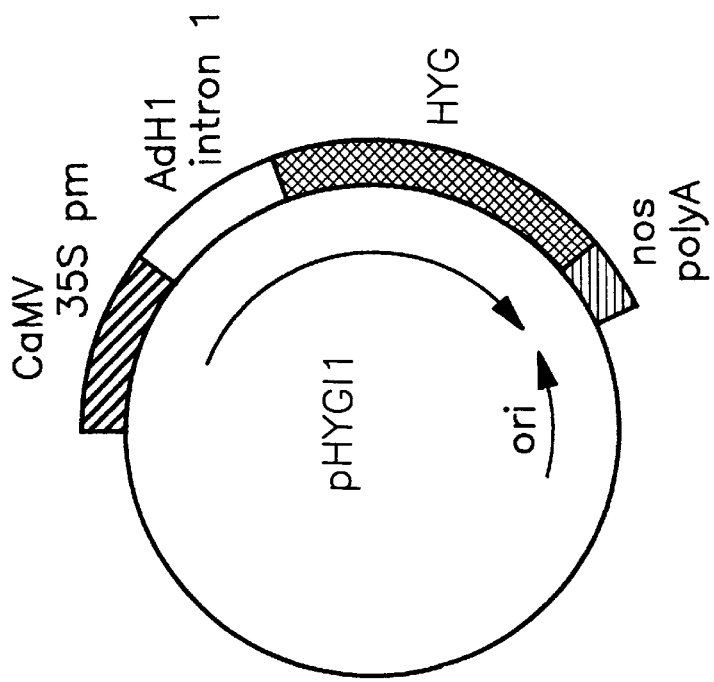
FIG. 1A shows a map of plasmid vector pHYGI1 utilized in Example I.

The present invention is directed to the production of fertile transgenic plants and seeds of the species Zea mays and to the plants, plant tissues, and seeds derived from such transgenic plants, as well as the subsequent progeny and products derived therefrom. The transgenic plants produced herein include all plants of this species, including field corn, popcorn, sweet corn, flint corn and dent corn.

"Transgenic" is used herein to include any cell, cell line, callus, tissue, plant part or plant which contains heterologous DNA that was introduced into plant material by a process of genetic engineering, or which was initially introduced into a plant species by such a process and was subsequently transferred to later generations by sexual or asexual cell crosses or cell divisions.

By "heritable" is meant that the DNA is capable of transmission through a complete sexual cycle of a plant, i.e. passed from one plant through its gametes to its progeny plants in the same manner as occurs in normal corn.

The transgenic plants of this invention may be produced by (i) establishing friable embryogenic callus from the plant to be transformed, (ii) transforming said cell line by a microprojectile bombardment technique, (iii) controllably identifying or selecting transformed cells, and (iv) regenerating fertile transgenic plants from the transformed cells. Some of the plants of this invention may be produced from the transgenic seed produced from the fertile transgenic plants using conventional crossbreeding techniques to develop commercial hybrid seed containing heterologous DNA.

I. Plant Lines and Tissue Cultures

The cells which have been found useful to produce the fertile transgenic maize plants herein are those callus cells which are regenerable, both before and after undergoing a selection regimen as detailed further below. Generally, these cells will be derived from meristematic tissue which contain cells which have not yet terminally differentiated. Such tissue in graminaceous cereals in general and in maize, in particular, comprise tissues found in juvenile leaf basal regions, immature tassels, immature embryos, and coleoptilar nodes. Preferably, immature embryos are used. Methods of preparing and maintaining callus from such tissue and plant types are well known in the art and details on so doing are available in the literature, c.f. Phillips et al. (1988), the disclosure of which is hereby incorporated by reference.

The specific callus used must be able to regenerate into a fertile plant. The specific regeneration capacity of particular callus is important to the success of the bombardment/selection process used herein because during and following selection, regeneration capacity may decrease significantly. It is therefore important to start with cultures that have as high a degree of regeneration capacity as possible. Callus which is more than about 3 months and up to about 36 months of age has been found to have a sufficiently high level of regenerability and thus is currently preferred. The regenerative capacity of a particular culture may be readily determined by transferring samples thereof to regeneration medium and monitoring the formation of shoots, roots, and plantlets. The relative number of plantlets arising per Petri dish or per gram fresh weight of tissue may be used as a rough quantitative estimate of reqeneration capacity. Generally, a culture which will produce at least one plant per gram of callus tissue will be preferred.

While maize callus cultures can be initiated from a number of different plant tissues, the cultures useful herein are preferably derived from immature maize embryos which are removed from the kernels of an ear when the embryos are about 1–3 mm in length. This length generally occurs about 9–14 days after pollination. Under aseptic conditions, the embryos are placed on conventional solid media with the embryo axis down (scutellum up). Callus tissue appears from the scutellum after several days to a few weeks. After the callus has grown sufficiently, the cell proliferations from the scutellum may be evaluated for friable consistency and the presence of well-defined embryos. By "friable consistency" is meant that the tissue is easily dispersed without causing injury to the cells. Tissue with this morphology is then transferred to fresh media and subcultured on a routine basis about every two weeks.

The callus initiation media is solid because callus cannot be readily initiated in liquid medium. The initiation/maintainence media is typically based on the N6 salts of Chu et al. (1975) as described in Armstrong et al. (1985) or the MS salts of Murashige et al. (1962). The basal medium is supplemented with sucrose and 2,4-dichlorophenoxyacetic acid (2,4-D). Supplements such as L-proline and casein hydrolysate have been found to improve the frequency of initiation of callus cultures, morphology, and growth. The cultures are generally maintained in the dark, though low light levels may also be used. The level of synthetic hormone 2,4-D, necessary for maintainence and propagation, should be generally about 0.3 to 3.0 mg/l.

Although successful transformation and regeneration has been accomplished herein with friable embryogenic callus, this is not meant to imply that other transformable regenerable cells, tissue, or organs cannot be employed to produce the fertile transgenic plants of this invention. The only actual requirement for the cells which are transformed is that after transformation they must be capable of regeneration of a plant containing the heterologous DNA following the particular selection or screening procedure actually used.

II. DNA Used for Transformation

The heterologous DNA used for transformation herein may be circular or linear, double-stranded or single-stranded. Generally, the DNA is in the form of a plasmid and contains coding regions of beneficial heterologous DNA with flanking regulatory sequences which serve to promote the expression of the heterologous DNA present in the resultant corn plant. "Heterologous DNA" is used herein to include all synthetically engineered or biologically derived DNA which is introduced into a plant by man by genetic engineering, including but not limited to, non-plant genes, modified genes, synthetic genes, portions of genes, as well as DNA and genes from maize and other plant species.

The compositions of and methods for constructing heterologous DNA for successful transformations of plants is well known to those skilled in the art, and the same compositions and methods of construction may be utilized to produce the heterologous DNA useful herein. The specific composition of the DNA is not central to the present invention and the invention is not dependent upon the composition of the specific transforming DNA used. weising et al. (1988), the subject matter of which is incorporated herein by reference, describes suitable DNA components thereof which include promoters, polyadenylation sequences, selectable marker genes, reporter genes, enhancers, introns, and the like, as well as provides suitable references for compositions thereof. Sambrook et al. (1989) provides suitable methods of construction.

Generally the heterologous DNA will be relatively small, i.e. less than about 30 kb to minimize any susceptibility to physical, chemical, or enzymatic degradation which is known to increase as the size of the DNA increases.

Suitable heterologous DNA for use herein includes all DNA which will provide for, or enhance, a beneficial feature of the resultant transgenic corn plant. For example, the DNA may encode proteins or antisense RNA transcripts in order to promote increased food values, higher yields, pest resistance, disease resistance, and the like. For example, a bacterial dap A gene for increased lysine; Bt-endotoxin gene or protease inhibitor for insect resistance; bacterial ESPS synthase for resistance to glyphosate herbicide; chitinase or glucan endo-1,3-B-glucosidase for fungicidal properties. Also, the DNA may be introduced to act as a genetic tool to generate mutants and/or assist in the identification, genetic tagging, or isolation of segments of corn DNA. Additional examples may be found in Table 1:

TABLE 1

| Eukaryotic genes transferred to higher plants | | | |
|---|---|---|---|
| Origin of gene | Transferred constructs | Transformed species | Mode of foreign gene expression |
| Animals | | | |
| Drosophila heat shock gene hsp 70 | 5' hsp70/nptII/3' ocs | tobacco (plants, tumors) | + temperature-dependent and organ-specific |
| Drosophila copia element LTR | 5' copia/cat | rice, wheat and sorghum (protoplasts) | (−) transient, but strong |

TABLE 1-continued

Eukaryotic genes transferred to higher plants

| Origin of gene | Transferred constructs | Transformed species | Mode of foreign gene expression |
| --- | --- | --- | --- |
| firefly luciferase gene | 5' CaMV 35S/luciferase cDNA/3' nos<br>5' CaMV 19S/luciferase cDNA/3' nos<br>5' deletion series | tobacco (plants)<br>carrot (protoplasts) | –<br>(+) transient |
| Rabbit β-globin gene | genomic | tobacco (tumors) | (–) not expressed |
| Human α-globin gene | 5' nos/α-globin | tobacco (plants) | (+) incorrect transcript processing |
| Chicken α-actin gene | genomic | tobacco (tumors) | (–) not expressed |
| Chicken oyalbumin gene | genomic | tobacco (tumors) | (+) incorrect transcript processing |
| Mouse metallothionein gene (mmt) | 5' mmt/cat | tobacco (tumors) | (–) not expressed |
| Mouse dihydrofolate reductase gene (DHFR) | 5' CaMV 35S/DHFR-cDNA/ 3' nos | Petunia (plants) | + expression confers methotrexate resistance |
| Human growth hormone gene (hgh) | 5' CaMV 35S/hgh | tobacco (plants, tumors) | (+) incorrect transcript processing |
| | 5' nos/hgh/3' nos | tobacco and sunflower (tumors) | (+) transcription, but neither processing nor translation |
| | 5' CaMV 35S/hgh/hgh 3' | tobacco (plants) | (+) incorrect transcript polyadenylation |
| SV40 early genes | 5' SV40/cat | tobacco (tumors) | (–) not expressed |
| | 5' CaMV 35S/cat/3' SV40 | tobacco (plants) | (+) incorrect transcript polyadenylation |
| HSV thymidine kinase gene (tk) | 5' HSV/tk/cat | tobacco (tumors) | (–) not expressed |
| Adenovirus type 5 EIA gene | 5' CaMV 35S/EIA/ 3' EIA/3' rbcS | tobacco (plants) | (+) termination within rbcS, EIA polyadenylation site not used |
| Yeast | | | |
| Yeast ADH | genomic | tobacco (plants) | (–) not expressed |
| Plant virus | | | |
| cDNA encoding TMV coat protein (tobacco mosaic virus) | 5' CaMV 35S/TMVcDNA/ 3' nos | tobacco (plants) | + expression confers enhanced resistance to TMV infection |
| cDNA encoding AMV coat protein (alfalfa mosaic virus) | 5' CaMV 19S/AMVcDNA 5' CaMV 3SS/AMVcDNA/ 3' nos. | tobacco and tomato (plants) | + expression confers enhanced resistance to AMV infection |
| cDNAs encoding A- and B- component of TGMV (tomato golden mosaic virus) | separate transformation with either A- or B-component via agroinfection | Petunia (plants) | + only A-components in tandem are able to replicate |
| cDNA encoding CMV (cucumber mosaic virus) satellite RNA | 5' CaMV 35S/CMVcDNA/ 3' nos | tobacco (plants) | + expression confers enhanced resistance to CMV infection |
| Plants | | | |
| Bean phaseolin gene | 5' ocs/phaseolin genomic<br>genomic | sunflower (tumors)<br>tobacco (plants) | + expressed and processed correctly<br>+ development-specific expression in seeds: targeting to protein bodies in endosperm and embryos |
| | 5' phaseolin/phaseolin- cDNA/3' phaseolin | tobacco (tumors) | + higher expression than using a genomic clone |
| | 5' phaseolin/maize zein/ 3' phaseolin | tobacco (plants) | + development-specific zein gene expression in tobacco seeds. Zein accumulation |
| Bean phytohemagglutinin-L gene (PHA-L) | genomic | tobacco (plants) | + development-specific expression in tobacco seeds |
| Soybean β-conglycinin gene (α subunit) | genomic<br>5' deletion series | Petunia (plants) | + development-specific expression in Petunia seeds depending on 5' sequences |
| | 5' CaMV 35S or 19S/ conglycinin/3' nos | Petunia (plants) | + constitutive expression: 35S> 19S; 20 fold clonal variation |
| Soybean β-conglycinin gene (β subunit) | genomic | tobacco and Petunia (plants) | + development-specific expression in seeds |
| Potato patatin gene | 5' patatin/cat/3' nos<br>5' ST-LS.1/patatin/3' patatin | potato (plants)<br>tobacco (plants) | + organ-specific expression in tubers<br>+ light-regulated and organ-specific expression depending on the ST-LS.1 promoter. Correct splicing of patatin mRNA. |
| Maize zein gene | genomic | sunflower (tumors) | (+) transcription, but no detectable protein |
| | 5' phaseolin/zein/3' phaseolin | tobacco (plants) | + development-specific expression in tobacco seeds |
| Wheat glutenin genes | 5' glutenin/cat/3' nos | tobacco (plants) | + development-specific expression |

TABLE 1-continued

Eukaryotic genes transferred to higher plants

| Origin of gene | Transferred constructs | Transformed species | Mode of foreign gene expression |
|---|---|---|---|
| | | | in tobacco seeds |
| Wheat chlorophyll a/b-binding protein (cab) gene | genomic | Petunia and tobacco plants | + light-regulated and organ-specific expression in leaves |
| | genomic<br>5' cab/cat<br>5' cab/5' CaMV 35S/cat/<br>3' rbcS<br>5' deletion series | tobacco (plants) | + phytochrome-regulated expression in leaves depending on 5' sequences |
| Pea cab gene | 5' cab/nptII<br>5' cab/5' nos/nptII | tobacco (plants) | + light-regulated, organ-and cell-specific expression; depending on enhancer/silencer-like 5, sequences. Involvement of phytochrome. Correlation to the presence of chloroplasts. |
| Petunia cab gene | 5' cab/ocs<br>5' cab/nos | Petunia and tobacco (plants) | + clonal variation of expression (200 fold) independent of copy number and homo-/heterologous host genome |
| Arabidopsis cab gene | 5' cab/cat | tobacco (plants) | + light-regulated and organ-specific expression |
| Pea ribulose 1.5-Bisphosphate carboxylase small subunit gene (rbcS) E9 | genomic<br>5' rbcS/cat<br>5' deletion series | Petunia (tumors) | + light-regulated expression dependent on 5' sequences |
| | genomic<br>5' deletion series | Petunia and tobacco (plants) | + light-regulated and organ-specific expression dependent on 5' sequences: 25-fold clonal variation |
| Pea rbcS 3.6 | 5' rbcS/cat/3' nos<br>5' deletion series | tobacco (tumors) | + light-regulated expression dependent on enhancer-like 5' sequences |
| | 5' rbcS/rbcS transit sequence/nptII | tobacco (tumors and plants) | + light-regulated expression and targeting of neomycin phosphotransferase into chloroplasts; analysis of signal sequences |
| | 5' rbcS/nptII | tobacco (plants) | + light-regulated, organ- and cell-specific expression. Involvement of a blue-light receptor |
| Pea rbcS 3A, 3C | genomic | Petunia (plants) | + regulation of transcription by phytochrome- and/or blue-light receptor depending on the developmental state |
| Pea rbcS 3A, E9 | 5' rbcS/5' CaMV 35S/cat<br>5' deletion series | Petunia and tobacco (plants) | + light-regulated and organ-specific expression depending on enhancer- and silencer-like 5' sequences |
| Soybean rbcS | 5' rbcS/nptII/3' ocs<br>5' rbcS/nos<br>5' rbcS/nptII/3' nos | soybean (tumors)<br>Kalanchoe (tumors)<br>Petunia (plants) | + light-regulated expression<br>+ light-regulated expression<br>+ light-regulated expression mediated by phytochrome |
| Soybean, pea and Petunia rbcS | 5' rbcS/nptII/3' nos | tomato (plants) | + expression stronger than directed by nos-promoter |
| Nicotiana plumbaginifolia rbcS 8B | 5' rbcS/cat | tobacco and Petunia (plants) | + light-regulated and organ-specific expression; 3-fold clonal variation independent of homo-/ heterologous host genome |
| Wheat rbcS | genomic<br>5' CaMV 35S/rbcS/3' rbcS | tobacco (plants) | (+) no expression under the control of wheat promoter; CaMV 35S promoter is necessary |
| Potato ST-LS.1 gene | genomic; modified by exon tagging | potato and tobacco (plants) | + light-regulated and organ-specific expression depending on the presence of chloroplasts and 5' sequences. Clonal variation parallels copy number, but is independent of homo-/ heterologous host. |
| | 5' ST-LS.1/patatin/3' patatin | tobacco (plants) | + light-regulated and organ-specific expression depending on the ST-L.1 promoter sequences |
| Petroselinum and Antirrhinum chalcone synthase genes (chs) | 5' chs(A)/nptII/3' chs(P)<br>5' deletion series | tobacco (plants) | + UV-B-light-regulated expression dependent on enhancer-like 5' sequences |

TABLE 1-continued

Eukaryotic genes transferred to higher plants

| Origin of gene | Transferred constructs | Transformed species | Mode of foreign gene expression |
| --- | --- | --- | --- |
| potato proteinase inhibitor II gene (PI II) | genomic<br>5' PI II/cat/3' T-DNA gene 6b<br>5' PI II/cat/3' PI II | tobacco (plants) | + wound-inducible expression depending on 5' and 3' sequences; systemic spreading by transacting factors |
| Soybean heat shock gene hs 6871 | genomic<br>5' deletion series | sunflower (tumors) and tobacco (plants) | + temperature-regulated expression depending on 5' sequences |
| Soybean heat shock gene Gmhsp 17.SE | genomic<br>5' deletion series | sunflower (tumors) | + expression regulated by temperature and presence of cadmium and arsenite depending on 5' sequences |
| Maize heat shock gene hsp70 | genomic | Petunia (plants) | + temperature-regulated expression |
| Maize alcohol dehydrogenase I gene (AdhI) | 5' CaMV 35S/cat/AdhI intron/ 3' rbcS | tobacco (plants) | (+) maize AdhI intron is not removed from the transcript |
|  | 5' AdhI/cat<br>5' ocs/5' AdhI/cat<br>5' CaMV 35S/5' AdhI/cat<br>5' AdhI deletion series | tobacco (plants) and maize (protoplasts) | (+) anaerobically inducible cat-expression dependent on 5' AdhI sequences only if additional CaMV- or ocs-promoter/enhancer sequences are present. |
| Maize sucrose synthase gene (ss) | 5' ss/nptII/3' ocs | wheat (protoplasts) | (+) transient expression |
|  | 5' ss/nptII | maize (protoplasts) | (+) transient expression suspension-culture derived but not in leaf-derived protoplasts |
| Soybean β-tubulin gene | genomic | tobacco (plants) | + |
| cowpea trypsin inhibitor gene (CpTI) | 5' CaMV 35S/CpTI/3' nos | tobacco (plants) | + expression enhances resistance to insect pests |
| Petunia EPSP synthase gene | 5' CaMV 35S/EPSP/3' nos | Petunia (plants) | + 35S-directed EPSP overproduction confers glyphosate tolerance |
|  | 5' T7-T-DNA/Petunia EPSP transit sequence/bacterial EPSP (aroA) coding region | tobacco (plants) | + expression of bacterial EPSP; targeting into chloroplasts; glyphosate tolerance |
| Soybean leghemoglobin gene lbc3 | genomic | tobacco (plants) | n.d. |
|  | 5' lbc3/cat/3' lbc3 | Lotus corniculatus (plants) | + development-specific and inducible expression only in nodules and only after infection by Rhizobium; dependence on 5' regulatory sequences |
| Nicatiana plumbaginifolia "insert 7" enhancer-like sequence | 5' insert 7/5' nos/nptII | tobacco (plants) | + transient protoplast-specific overexpression of nptII |
| Nicotiana plumbaginifolia ATP synthase gene (atp2-1); β subunit | 5' CaMV 35S/atp2-1 signal sequence/cat | tobacco (plants) | + cat enzyme is targeted into mitochondria |
| Maize transposable elements Ac and Ds | Ac or Ds within borders of waxy locus | tobacco (tumors and shoots) | + Ac is capable of self-catalyzed transposition |

Abbreviations:
copia LTR - long terminal repeat of copia taansposable element
HSV - Herpes simplex virus
Adh - alcohol dehydrogenase gene
ST-LS 1 - Solanum ruberosum leaf/stem-specific gene
EPSP - 5 -enolpyruvylshikimate-3-phosphate (gene)
lbc3 - member of the leghemoglobin gene family
Ac, Ds - maize transposable elements (activator, dissociation)
rbcS - ribulose-1,5-bisphosphate carboxylase small subunit gene
cab - chlorophyl a/b binding protein gene
nptII - neomycin phosphotransferase II gene
ocs - octopine synthase gene
nos - nopaline synthase gene
cat - chloramphenicol acetyltransferase gene
CaMV 35S, 19S - cauliflower mosaic virus genes encoding 35S and 19S-transcript, respectively
genomic - transferred construct contains the entire gene including 5' and 3' regions
Mode of expression:
+ - correct expression of stably integrated gene
(+) - transient expression, or transcription followed by incorrect processing and/or translation
(−) - gene is not transcribed The heterologous DNA to be introduced into the plant further will generally contain either a selectable marker or a reporter gene or both to facilitate identification and selection of transformed cells. Alternatively, the selectable marker may be carried on a separate piece of DNA and used in a cotransformation procedure. Both selectable markers and reporter genes may be flanked with appropriate regulatory sequnces to enable expression in plants. Useful selectable markers are well known in the art and include, for example, antibiotic and herbicide resistance genes. Specific examples of such genes are disclosed in Table 2:

genes which confer herbicide resistance or tolerance are also of commercial utility in the resulting transformed plants.

Reporter genes which encode for easily assayable marker proteins are well known in the art. In general, a reporter gene is a gene which is not present or expressed by the recipient

TABLE 2

Selectable marker and reporter genes in plant genetic transformation

| Gene | Origin | Encoded enzyme | Useful as Selectable marker | Useful as Scorable reporter | Resistance against |
|---|---|---|---|---|---|
| Neomycin phosphotransferase gene II (nptII) | TnS | ncomycin phosphotransferase | ++ | + | ncomycin kanamycin G-418[1] |
| Neomycin phosphotransferase gene I (nptI) | Nn601 | ncomycin phosphotransferase | + | + | ncomycin kanamycin G-418[2] |
| Chloramphenicol acetyltransferase gene (cat) | Tn9 | chloramphenicol acetyltransferase | (+) | ++ | chloramphenicol[3] |
| Bacterial DHPR gene | plasmid R67 | dihydrofolate reductase | + | + | methotrexate[4] |
| Mutatcd c-DNA of a mouse DHFR gene | mouse | dihydrofolate reductase | ++ | + | methotrexate[5] |
| Octopine synthase gene (ocs) | T-DNA | octopine synthase | + | ++ | toxic opine precursor analogues, i.e. aminoethylcystein[6] |
| Nopaline synthase gene (nos) | T-DNA | nopaline synthase | – | ++ | —[7] |
| Hygromycin phosphotransferase gene (hpt) | E. coli | hygromycin phosphotransferase | ++ | – | hygromycin B[8] |
| Bicomycin resistance gene | Tn5 | ? | + | – | bicomycin[9] |
| Streptomycin phosphotransferase gene | Tn5 | streptomycin phosphotransferase | (+) | (+) | streptomycin[10] |
| | | | | control plants are not killed by streptomycin | |
| aroA gene | *Salmonella tryphimurium* | EPSP synthase | ++ | – | glyphosate[11] |
| bar gene | *Streptomices hygroscopicus* | phosphinothricin acetyltransferase | ++ | – | phosphinothricin, bialaphos[12] |
| β-galactosidase gene | E. coli | β-galactosidase | – | + | —[13] |
| Glucuronidase gene (GUS) | E. coli | glucuronidase | – | ++ | —[14] |
| Bacterial luciterase gene | Vibrso harvest | luciferase | – | ++ | —[15] |
| Firefly luciferase gene | *Photinus peralis* | luciferase | – | ++ | —[16] |

Only some representative references were chosen in case of the nptII, nos, ocs and cat genes.
Abbreviations
Tn - transpuson
DHFR - dihydrofolate reductase
EPSP synthase - 5-enolpyruvylskikimate-3-phosphate synthase
[1]M. Bevran et al., Nature, 304, 185 (1983); M. DeBlock et al., EMBOJ., 8, 1681 (1984); I. Herrera-Estrella et al., EMBOJ., 2, 987 (1983).
[2]R.T. Fraley et al., PNASUSA, 80, 1803 (1983); H. Pretrzak et al., Nucl, Acids Res., 14, 5857 (1986).
[3]M. DeBlock et al., EMBO J., 3, 1681 (1984); I. Herrera-Estrella et al., Nature, 303, 209 (1983).
[4]N. Brisson et al., Nature, 310, 511 (1984); M. DeBlock et al., ibid., I. Herrera-Estrella et al., EMBO J., 2, 987 (1983).
[5]D.A. Eichholtz et al., Somat. Cell, Mol. Genet., 13, 67 (1987).
[6]G.A. Dahl et al., Theor, Appl. Genet., 66, 233 (1983); H. DeGeve et al., Nature, 300, 752 (1982); A. Hockema et al., Plant Mol. Biol., 5, 85 (1985): M.G. Koztel et al., J. Mol. Appl. Genet., 2, 549 (1981).
[7]J.D.G. Jones et al., EMBO J., 4, 2411 (1985); C.H. Shaw et al., Nuc. Acids Res., 14, 6003 (1986); P. Zambryska et al., EMBO J., 2, 2443 (1983).
[8]A.M. Lloyd et al., Science, 284, 464 (1986); P.I.M. Van den Hazen et al., Plant MOl. Biol., 5, 299 (1985); C. Waldron et al., Plant Mol. Biol., 5, 103 (1985).
[9]J. Hille et al., Plant Mol. Biol., 2, 171 (1986).
[10]J.D.G. Jones et al., Mol. Gen. Genet., 210, 86 (1987).
[11]L. Comai et al., Nature, 317, 741 (1985); J.J. Inllatti et al., Biotechnology, 5, 726 (1987).
[12]M. DeBlock et al., EMBO J., 6, 2513 (1987); C.T. Thompson et al., EMBO J., 6, 2519 (1987).
[13]G. Heimer et al., Biotechnology, 2, 520 (1984).
[14]D.R. Gallic et al., Nuc. Acids Res., 15, 8693 (1987); R.A. Jefferson et al., EMBO J., 6, 1901 (1987).
[15]C. Koncz et al., Mol. Gen. Genet., 204, 383 (1986).
[16]D.W. Ow et al., Science, 234, 856 (1986); D.W. Ow et al., PNAS USA, 84, 4870 (1987); C.D. Riggs et al., Nucl. Acids Res., 15, 8115 (1987).

A preferred selectable marker gene is the hygromycin B phosphotransferase (HPT) coding sequence, which may be derived from E. coli. Other selectable markers known in the art include aminoglycoside phosphotransferase gene of transposon Tn5 (AphII) which encodes resistance to the antibiotics kanamycin, neomycin, and G418, as well as those genes which code for resistance or tolerance to glyphosate, methotrexate, imidazolinones, sulfonylureas, bromoxynil, dalapon, and the like. Those selectable marker organism or tissue and which encodes a protein whose expression is manifested by some easily detectable property, e.g. phenotypic change or enzymatic activity. Examples of such genes are provided in Table 2. Preferred genes include the chloramphenicol acetyl transferase gene from Tn9 of E. coli, the beta-glucuronidase gene of the uida locus of E. coli, and the luciferase genes from firefly Photinus pyralis.

The regulatory sequences useful herein include any constitutive, inducible, tissue or organ specific, or developmental stage specific promoter which can be expressed in the particular plant cell. Suitable such promoters are disclosed in Weising et al, supra. The following is a partial representative list of promoters suitable for use herein: regulatory sequences from the T-DNA of *Agrobacterium tumefaciens*, including mannopine synthase, nopaline synthase, and octopine synthase; alcohol dehydrogenase promoter from corn; light inducible promoters such as, ribulose-biphosphate-carboxylase small subunit gene from a variety of species; and the major chlorophyll a/b binding protein gene promoter; 35s and 19S promoters of cauliflower mosaic virus; developmentally regulated promoters such as the waxy, zein, or bronze promoters from maize; as well as synthetic or other natural promoters which are either inducible or constitutive, including those promoters exhibiting organ specific expression or expression at specific development stage(s) of the plant.

Other elements such as introns, enhancers, polyadenylation sequences and the like, may also be present on the DNA. Such elements may or may not be necessary for the function of the DNA, although they can provide a better expression or functioning of the DNA by affecting transcription, stability of the mRNA, or the like. Such elements may be included in the DNA as desired to obtain the optimal performance of the transforming DNA in the plant. For example, the maize Adh1S first intron may be placed between the promoter and the coding sequence of a particular heterologous DNA. This intron, when included in a DNA construction, is known to generally increase expression in maize cells of a protein. (Callis et al. 1987) However, sufficient expression for a selectable marker to perform satisfactorily can often be obtained without an intron. (Klein et al. 1989) An example of an alternative suitable intron is the shrunken-1 first intron of *Zea mays*. These other elements must be compatible with the remainder of the DNA constructions.

To determine whether a particular combination of DNA and recipient plant cells are suitable for use herein, the DNA may include a reporter gene. An assay for expression of the reporter gene may then be performed at a suitable time after the DNA has been introduced into the recipient cells. A preferred such assay entails the use of the *E. coli* beta-glucuronidase (GUS) gene (Jefferson et al. 1987). In the case of the microprojectile bombardment transformation process of the present invention, a suitable time for conducting the assay is about 2–3 days after bombardment. The use of transient assays is particularly important when using DNA components which have not previously been demonstrated or confirmed as compatible with the desired recipient cells.

III. DNA Delivery Process

The DNA can be introduced into the regenerable maize callus cultures via a particle bombardment process. A general description of a suitable particle bombardment instrument is provided in Sanford et al. (1987), the disclosure of which is incorporated herein by reference. While protocols for the use of the instrument in the bombardment of maize non-regenerable suspension culture cells are described in Klein et al. (1988a, 1988b, and 1989), no protocols have been published for the bombardment of callus cultures or regenerable maize cells.

In a microprojectile bombardment process, also referred to as a biolistic process, the transport of the DNA into the callus is mediated by very small particles of a biologically inert material. When the inert particles are coated with DNA and accelerated to a suitable velocity, one or more of the particles is able to enter into one or more of the cells where the DNA is released from the particle and expressed within the cell. While some of the cells are fatally damaged by the bombardment process, some of the recipient cells do survive, stably retain the introduced DNA, and express it.

The particles, called microprojectiles, are generally of a high density material such as tungsten or gold. They are coated with the DNA of interest. The microprojectiles are then placed onto the surface of a macroprojectile which serves to transfer the motive force from a suitable energy source to the microprojectiles. After the macroprojectile and the microprojectiles are accelerated to the proper velocity, they contact a blocking device which prevents the macroprojectile from continuing its forward path but allows the DNA-coated microprojectiles to continue on and impact the recipient callus cells. Suitable such instruments may use a variety of motive forces such as gunpowder or shock waves from an electric arc discharge (Swain et al. 1988). An instrument in which gunpowder is the motive force is currently preferred and such is described and further explained in Sanford et al. (1987), the disclosure of which is incorporated herein by reference.

A protocol for the use of the gunpowder instrument is provided in Klein et al. (1988a, b) and involves two major steps. First, tungsten microprojectiles are mixed with the DNA, calcium chloride, and spermidine free base in a specified order in an aqueous solution. The concentrations of the various componenets may be varied as taught. The currently preferred procedure entails exactly the procedure of Klein et al. (1988b) except for doubling the stated optimum DNA concentration. Secondly, in the actual bombardment, the distance of the recipient cells from the end of the barrel as well as the vacuum in the sample chamber. The currently preferred procedure for bombarding the callus entails exactly the procedure of Klein et al. (1988b) with the recipient tissue positioned 5 cm below the stopping plate tray.

The callus cultures useful herein for generation of transgenic plants should generally be about 3 months to 3 years old, preferably about 3 to 18 months old. Callus used for bombardment should generally be about midway between transfer periods and thus past any "lag" phase that might be associated with a transfer to a new media, but also before reaching any "stationary" phase associated with a long time on the same plate.

The specific tissue subjected to the bombardment process is preferably taken about 7–10 days after subculture, though this is not believed critical. The tissue should generally be used in the form of pieces of about 30 to 80, preferably about 40 to 60, mg. The clumps are placed on a petri dish or other surface and arranged in essentially any manner, recognizing that (i) the space in the center of the dish will receive the heaviest concentration of metal-DNA particles and the tissue located there is likely to suffer damage during bombardment and (ii) the number of particles reaching a cell will decrease (probably exponentially) with increasing distance of the cell from the center of the blast so that cells far from the center of the dish are not likely to be bombarded and transformed. A mesh screen, preferably of metal, may be laid on the dish to prevent splashing or ejection of the tissue. The tissue may be bombarded one or more times with the DNA-coated metal particles.

IV. Selection Process

Once the calli have been bombarded with the DNA and the DNA has penetrated some of the cells, it is necessary to identify and select those cells which both contain the heterologous DNA and still retain sufficient regenerative capacity. There are two general approaches which have been found useful for accomplishing this. First, the transformed calli or plants regenerated therefrom can be screened for the presence of the heterologous DNA by various standard methods which could include assays for the expression of reporter genes or assessment of phenotypic effects of the heterologous DNA, if any. Alternatively and preferably, when a selectable marker gene has been transmitted along with or as part of the heterologous DNA, those cells of the callus which have been transformed can be identified by the use of a selective agent to detect expression of the selectable marker gene.

Selection of the putative transformants is a critical part of the successful transformation process since selection conditions must be chosen so as to allow growth and accumulation of the transformed cells while simultaneously inhibiting the growth of the non-transformed cells. The situation is complicated by the fact that the vitality of individual cells in a population is often highly dependent on the vitality of neighboring cells. Also, the selection conditions must not be so severe that the plant regeneration capacity of the callus cells and the fertility of the resulting plant are precluded. Thus the effects of the selection agent on cell viability and morphology should be evaluated. This may be accomplished by experimentally producing a growth inhibition curve for the given selective agent and tissue being transformed beforehand. This will establish the concentration range which will inhibit growth.

When a selectable marker gene has been used, the callus clumps may be either allowed to recover from the bombardment on non-selective media or, preferably, directly transferred to media containing that agent.

Selection procedures involve exposure to a toxic agent and may employ sequential changes in the concentration of the agent and multiple rounds of selection. The particular concentrations and cycle lengths are likely to need to be varied for each particular agent. A currently preferred selection procedure entails using an initial selection round at a relatively low toxic agent concentration and then later round(s) at higher concentration(s). This allows the selective agent to exert its toxic effect slowly over a longer period of time. Preferably the concentration of the agent is initially such that about a 5–40% level of growth inhibition will occur, as determined from a growth inhibition curve. The effect may be to allow the transformed cells to preferentially grow and divide while inhibiting untransformed cells, but not to the extent that growth of the transformed cells is prevented. Once the few individual transformed cells have grown sufficiently the tissue may be shifted to media containing a higher concentration of the toxic agent to kill essentially all untransformed cells. The shift to the higher concentration also reduces the possibility of non-transformed cells habituating to the agent. The higher level is preferably in the range of about 30 to 100% growth inhibition. The length of the first selection cycle may be from about 1 to 4 weeks, preferably about 2 weeks. Later selection cycles may be from about 1 to about 12 weeks, preferably about 2 to about 10 weeks. Putative maize transformants can generally be identified as proliferating sectors of tissue among a background of non-proliferating cells. The callus may also be cultured on non-selective media at various times during the overall selection procedure.

Once a callus sector is identified as a putative transformant, transformation can be confirmed by phenotypic and/or genotypic analysis. If a selection agent is used, an example of phenotypic analysis is to measure the increase in fresh weight of the putative transformant as compared to a control on various levels of the selective agent. Other analyses that may be employed will depend on the function of the heterologous DNA. For example, if an enzyme or protein is encoded by the DNA, enzymatic or immunological assays specific for the particular enzyme or protein may be used. Other gene products may be assayed by using a suitable bioassay or chemical assay. Other such techniques are well known in the art and are not repeated here. The presence of the gene can also be confirmed by conventional procedures, i.e. Southern blot or polymerase chain reaction (PCR) or the like.

V. Regeneration of Plants and Production of Seed

Cell lines which have been shown to be transformed must then be regenerated into plants and the fertility of the resultant plants determined. Transformed lines which test positive by genotypic and/or phenotypic analysis are then placed on a media which promotes tissue differentiation and plant regeneration. Regeneration may be carried out in accordance with standard procedures well known in the art. The procedures commonly entail reducing the level of auxin which discontinues proliferation of a callus and promotes somatic embryo development or other tissue differentiation. One example of such a regeneration procedure is described in Green et al. (1981). The plants are grown to maturity in a growth room or greenhouse and appropriate sexual crosses and selfs are made as described by Neuffer (1981).

Regeneration, while important to the present invention, may be performed in any conventional manner. If a selectable marker has been transformed into the cells, the selection agent may be incorporated into the regeneration media to further confirm that the regenerated plantlets are transformed. Since regeneration techniques are well known and not critical to the present invention, any technique which accomplishes the regeneration and produces fertile plants may be used.

VI. Analysis of R1 Progeny

The plants regenerated from the transformed callus are referred to as the R0 generation or R0 plants. The seeds produced by various sexual crosses of the R0 generation plants are referred to as R1 progeny or the R1 generation. When R1 seeds are germinated, the resulting plants are also referred to as the R1 generation.

To confirm the successful transmission and inheritance of the heterologous DNA in the sexual crosses described above, the R1 generation should be analyzed to confirm the presence of the transforming DNA. The analysis may be performed in any of the manners such as were disclosed above for analyzing the bombarded callus for evidence of transformation, taking into account the fact that plants and plant parts are being used in place of the callus.

VII. Breeding of Genetically Engineered Commercial Hybrid Seed

Generally, the commercial value of the transformed corn produced herein will be greatest if the heterologous DNA can be incorporated into many different hybrid combinations. A farmer typically grows several varieties of hybrids based on differences in maturity, standability, and other agronomic traits. Also, the farmer must select a hybrid based upon his physical location since hybrids adapted to one part of the corn belt are generally not adapted to another part because of differences in such traits as maturity, disease, and insect resistance. As such, it is necessary to incorporate the heterologous DNA into a large number of parental lines so that many hybrid combinations can be produced containing the desirable heterologous DNA. This may conveniently be done by breeding programs in which a conversion process (backcrossing) is performed by crossing the initial transgenic fertile plant to normal elite inbred lines and then crossing the progeny back to the normal parent. The progeny from this cross will segregate such that some of the plants will carry the heterologous DNA whereas some will not. The plants that do carry the DNA are then crossed again to the normal plant resulting in progeny which segregate once more. This crossing is repeated until the original normal parent has been converted to a genetically engineered line containing the heterologous DNA and also possessing all other important attributes originally found in the parent. A separate back-crossing program will be used for every elite line that is to be converted to a genetically engineered elite line. It may be necessary for both parents of a hybrid seed corn to be homozygous for the heterologous DNA. Corn breeding and the techniques and skills required to transfer genes from one line or variety to another are well-known to those skilled in the art. Thus introducing heterologous DNA into lines or varieties which do not generate the appropriate calli can be readily accomplished by these breeding procedures.

VIII. Uses of Transgenic Plants

The transgenic plants produced herein are expected to be useful for a variety of commercial and research purposes.

Transgenic plants can be created for use in traditional agriculture to possess traits beneficial to the grower (e.g. agronomic traits such as pest resistance or increased yield), beneficial to the consumer of the grain harvested from the plant (e.g. improved nutritive content in human food or animal feed), or beneficial to the food processor (e.g. improved processing traits). In such uses, the plants are generally grown for the use of their grain in human or animal foods. however, other parts of the plants, including stalks, husks, vegetative parts, and the like, may also have utility, including use as part of animal silaage or for ornamental purposes (e.g. Indian corn). often chemical constituents (e.g. oils or starches) of corn and other crops are extracted for food or in dustrial use and transgenic plants may be created which have enhanced or modified levels of such components. The plants may also be used for seed production for a variety of purposes.

Transgenic plants may also find use in the commercial manufacture of proteins or othermolecules encoded by the heterologous DNA contained therein, where the molecule of interest is extracted or purified from plant parts, seeds, and the like. Cells or tissue from the plants may also be cultured, grown in vitro, or fermented to manufacture such molecules, or for other purposes (e.g. for research).

The transgenic plants may also be used in commercial breeding programs, or may be crossed or bred to plants of related crop species. Improvements encoded by the heterologous DNA may be transferred, e.g. from corn cells to cells of other species e.g. by protoplast fusion.

The transgenic plants may have many use s in research or breeding, including creation of new mutant plants through insertional mutagenesis, in order to identify beneficial mutants that might later be created by traditional mutation and selection. The methods of the invention may also be used to create plants having unique "signature sequences" or other marker sequences which can be used to identify proprietary lines or varieties.

The following non-limiting examples are illustrative of the present invention. They are presented to better explain the general procedures which were used to prepare the fertile Zea mays plants of this invention which stably express the heterologous DNA and which transmit that DNA to progeny. All parts and percents are by weight unless otherwise specified. It must be recognized that a specific transformation event is a function of the amount of material subjected to the transformation procedure. Thus when individual situations arise in which the procedures described herein do not produce a transformed product, repetition of the procedures will be required.

EXAMPLE I

Fertile transgenic Zea mays plants which contain heterologous DNA which is heritable were prepared as follows:
I. Initiation and Maintenance of Maize Cell Cultures which Retain Plant Regeneration Capacity Friable, embryogenic maize callus cultures were initiated from hybrid immature embryos produced by pollination of inbred line A188 plants (University of Minnesota, Crop Improvement Association) with pollen of inbred line B73 plants (Iowa State University). Ears were harvested when the embryos had reached a length of 1.5 to 2.0 mm. The whole ear was surface sterilized in 50% v/v commercial bleach (2.63% w/v sodium hypochlorite) for 20 min. at room temperature. The ears were then washed with sterile distilled, deionized water. Immature embryos were aseptically isolated and placed on nutrient agar initiation/maintenance media with the root/shoot axis exposed to the medium. Initiation/maintenance media (hereinafter refered to as F medium) consisted of N6 basal media (Chu 1975) with 2% (w/v) sucrose, 1.5 mg per liter 2,4-dichlorophenoxyacetic acid (2,4-D), 6 mM proline, and 0.25% Gelrite (Kelco, Inc. San Diego). The pH was adjusted to 5.8 prior to autoclaving. Unless otherwise stated, all tissue culture manipulations were carried out under sterile conditions.

The immature embryos were incubated at 26° C. in the dark. Cell proliferations from the scutellum of the immature embryos were evaluated for friable consistency and the presence of well defined somatic embryos. Tissue with this morphology was transferred to fresh media 10 to 14 days after the initial plating of the immature embryos. The tissue was then subcultured on a routine basis every 14 to 21 days. Sixty to eighty milligram quantities of tissue were removed from pieces of tissue that had reached a size of approximately one gram and transferred to fresh media. Subculturing always involved careful visual monitoring to be sure that only tissue of the correct morphology was maintained. The presence of somatic embryos ensured that the cultures would give rise to plants under the proper conditions. The cell culture named AB12 used in this example was such a culture and had been initiated about 1 year before bombardment.

II. Plasmids—pCHN1-1, pHYGI1, pBII221, and pLUC-1

Figure 1B:
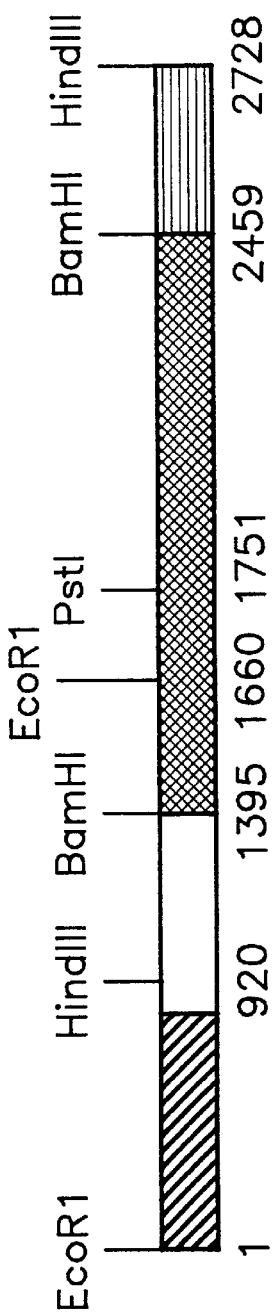
FIG. 1B shows the relevant part of pHYGI1 encompassing the HPT coding sequence and associated regulatory elements. The base pair numbers start from the 5' nucleotide in the recognition sequence for the indicated restriction enzymes, beginning with the EcoRI site at the 5' end of the CaMV 35S promoter.
Figure 2A:
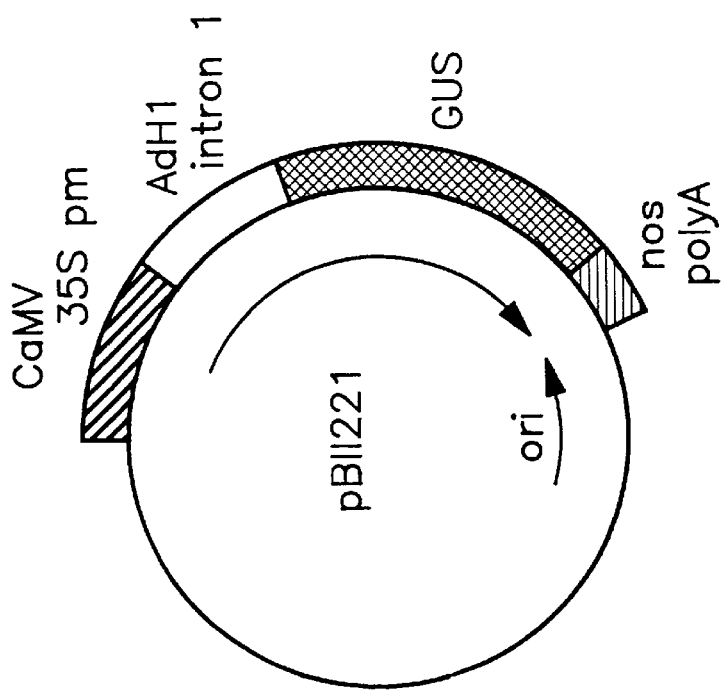
FIG. 2 shows a map of plasmid vector pBII221 utilized in Example I.
Figure 2B:
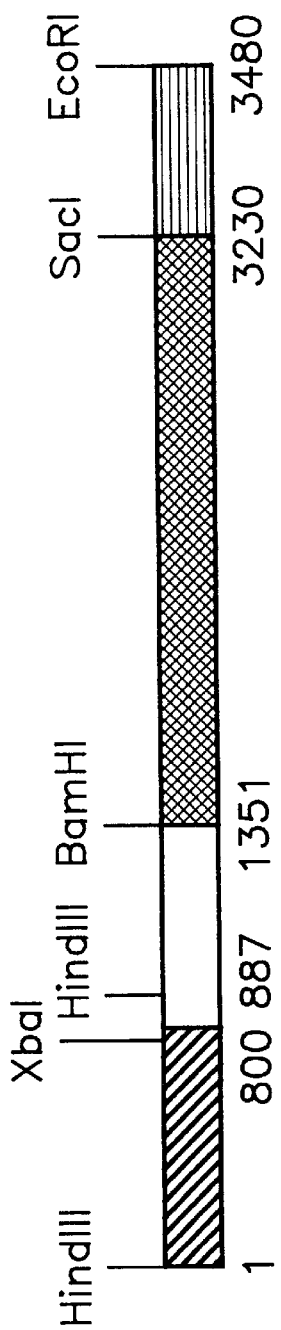

The plasmids pCHN1-1, pHYGI1, and pLUC-1 were constructed in the vector pBS+ (Stratagene, Inc., San Diego, Calif.), a 3.2 Kb circular plasmid, using standard recombinant DNA techniques. pCHN1-1 contains the hygromycin B phosphotransferase (HPT) coding sequence from E. coli (Gritz et al. 1983) flanked at the 3' end by the nopaline synthase (nos) polyadenylation sequence of Agrobacterium tumefaciens (Chilton and Barnes 1983). Expression is driven by the cauliflower mosaic virus (CaMV) 35S promoter (Guilley et al. 1982), located upstream from the hygromycin coding sequence. The plasmid pHYGI1 was constructed by inserting the 553 bp Bcl-BamHI fragment containing the maize Adh1S first intron (Callis et al. 1987) between the CaMV 35S promoter and the hygromycin coding sequence of pCHN1-1. A map of pHYGI1 is provided as FIG. 1.

pBII221 contains the E. Coli B-glucuronidase coding sequence flanked at the 5' end by the CaMV 35S promoter and at the 3' end by the nos polyadenylation sequence. The plasmid was constructed by inserting the maize AdhIS first intron between the 35S promoter and the coding sequence of pBI221 (Jefferson et al. 1987). A map of pBII221 is provided as FIG. 2.

pLUC-1 contains the firefly luciferase coding sequence (DeWet et al. 1987) flanked at the 5' end by the CaMV 35S promoter and at the 3' end by the nos polyadenylation sequence. This plasmid was used solely as a negative control.

Plasmids were introduced into the embryogenic callus culture AB12 by microprojectile bombardment.

III. DNA Delivery Process

The embryogenic maize callus line AB12 was subcultured 7 to 12 d prior to microprojectile bombardment. AB12 was prepared for bombardment as follows. Five clumps of callus, each approximately 50 mg in wet weight were arranged in a cross pattern in the center of a sterile 60×15 mm petri plate (Falcon 1007). Plates were stored in a closed container with moist paper towels throughout the bombardment process. Twenty six plates were prepared.

Plasmids were coated onto M-10 tungsten particles (Biolistics) exactly as described by Klein, et al (1988b) except that, (i) twice the recommended quantity of DNA was used, (ii) the DNA precipitation onto the particles was performed at 0° C., and (iii) the tubes containing the DNA-coated tungsten particles were stored on ice throughout the bombardment process.

All of the tubes contained 25 ul 50 mg/ml M-10 tungsten in water, 25 ul 2.5 M $CaCl_2$, and 10 ul 100 mM spermidine free base along with a total of 5 ul 1 mg/ml total plasmid content. When two plasmids were used simultaneously, each was present in an amount of 2.5 ul. One tube contained only plasmid pBII221; two tubes contained both plasmids pHYGI1 and pBII221; two tubes contained both plasmids pCHNl-1 and pBII221; and one tube contained only plasmid pLUC-1.

All tubes were incubated on ice for 10 min., pelletized by centrifugation in an Eppendorf centrifuge at room temperature for 5 seconds, and 25 ul of the supernatant was discarded. The tubes were stored on ice throughout the bombardment process. Each preparation was used for no more than 5 bombardments.

Macroprojectiles and stopping plates were obtained from Biolistics, Inc. (Ithaca, N.Y.). They were sterilized as described by the supplier. The microprojectile bombardment instrument was obtained from Biolistics, Inc.

The sample plate tray was positioned at the position 5 cm below the bottom of the stopping plate tray of the microprojectile instrument, with the stopping plate in the slot below the barrel. Plates of callus tissue prepared as described above were centered on the sample plate tray and the petri dish lid removed. A 7×7 cm square rigid wire mesh with 3×3 mm mesh and made of galvanized steel was placed over the open dish in order to retain the tissue during the bombardment. Tungsten/DNA preparations were sonicated as described by Biolistics, Inc. and 2.5 ul was pipetted onto the top of the macroprojectiles. The instrument was operated as described by the manufacturer. The following bombardments were performed:

2×pBII221 prep To determine transient expression frequency

10×pHYGI1/pBII221 As a potential positive treatment for transformation

10×pCHN1-1/pBII221 As a potential positive treatment for transformation

4×pLUC-1 Negative control treatment

The two plates of callus bombarded with pBII221 were transferred plate for plate to F medium (with no hygromycin) and the callus cultured at 26° C. in the dark. After 2 d this callus was then transferred plate for plate into 35×10 mm petri plates (Falcon 1008) containing 2 ml of GUS assay buffer which consists of 1 mg/ml 5-bromo-4-chloro-3-indolyl-beta-D-glucuronide (Research Organics), 100 mM sodium phosphate pH 7.0, 5 mM each of potassium ferricyanide and potassium ferrocyanide, 10 mM EDTA, and 0.06% Triton X-100. These were incubated at 37° C. for 3 d after which the number of blue cells was counted giving 291 and 477 transient GUS expressing cells in the two plates, suggesting that the DNA delivery process had also occurred with the other bombarded plates. These plates were discarded after counting since the GUS assay is destructive.

IV. Selection Process

Hygromycin B (Calbiochem) was incorporated into the medium by addition of the appropriate volume of filter sterilized 100 mg/ml Hygromycin B in water when the media had cooled to 45° C. prior to pouring plates.

Immediately after all samples had been bombarded, callus from all of the plates treated with pHYGI1/pBII221, pCHN1-1/pBII221 and three of the plates treated with pLUC-1 were transferred plate for plate onto F medium containing 15 mg/l hygromycin B, (five pieces of callus per plate). These are referred to as round 1 selection plates. Callus from the fourth plate treated with pLUC-1 was transferred to F medium without hygromycin. This tissue was subcultured every 2–3 weeks onto nonselective medium and is referred to as unselected control callus.

After two weeks of selection, tissue appeared essentially identical on both selective and nonselective media. All callus from eight plates from each of the pHYGI1/pBII221 and pCHN1-1/pBII221 treatments and two plates of the control callus on selective media were transferred from round 1 selection plates to round 2 selection plates that contained 60 mg/l hygromycin. The round 2 selection plates each contained ten 30 mg pieces of callus per plate, resulting in an expansion of the total number of plates.

The remaining tissue on selective media, two plates each of pHYGI1/pBII221 and pCHN1-1/pBII221 treated tissue and one of control callus, were placed in GUS assay buffer at 37° C. to determine whether blue clusters of cells were observable at two weeks post-bombardment. After 6 d in assay buffer this tissue was scored for GUS expression.

| TREATMENT | REPLICATE | OBSERVATIONS |
|---|---|---|
| pLUC-1 | | no blue cells |
| pHYGI1/pBII221 | plate 1 | 11 single cells |
| | | 1 four cell cluster |
| | plate 2 | 5 single cells |
| pCHN1-1/pBII221 | plate 1 | 1 single cell |
| | | 2 two cell clusters |
| | plate 2 | 5 single cells |
| | | 1 two cell cluster |
| | | 2 clusters of 8–10 cells |

After 21 d on the round 2 selection plates, all viable portions of the material were transferred to round 3 selection plates containing 60 mg/l hygromycin. The round 2 selection plates, containing only tissue that was apparently dead, were reserved. Both round 2 and 3 selection plates were observed periodically for viable proliferating sectors.

After 35 d on round 3 selection plates both the round 2 and round 3 sets of selection plates were checked for viable sectors of callus. Two such sectors were observed proliferating from a background of dead tissue on plates treated with pHYGI1/pBII221. The first sector named 3AA was from the round 3 group of plates and the second sector named 6L was from the round 2 group of plates. Both lines were then transferred to F medium without hygromycin.

After 19 d on F medium without hygromycin the line 3AA grew very little whereas the line 6L grew rapidly. Both were transferred again to F medium for 9 d. The lines 3AA and 6L were then transfered to F medium containing 15 mg/l hygromycin for 14 d. At this point, line 3AA was observed to be of very poor quality and slow growing. The line 6L however grew rapidly on F medium with 15 mg.l hygromycin. In preparation for an inhibition study of the line 6L on hygromycin, the line was then subcultured to F medium without hygromycin.

After 10 d on F medium an inhibition study of the line 6L was initiated. Callus of 6L was transfered onto F medium containing 0, 10, 30, 100, and 250 mg/l hygromycin B. Five plates of callus were prepared f or each concentration and each plate contained ten approximately 50 mg pieces of callus. one plate of unselected control ti ssue was prepared for each concentration of hygromycin.

It was found that the line 6L was capable of sustained growth over 9 subcultures on 0, 10, 30, 100, and 250 mg/l hygromycin. The name of the line 6L was changed at this time from 6L to PH1 (Positive Hlygromycin transformant 1).

Additional sectors were recovered at various time points from the round 2 and 3 selection plates. None of these were able to grow in the presence of hygromycin for multiple rounds, i.e. two or three subcultures.

V. Confirmation of transformed callus

To show that the PHi callus had acquired the hygromycin resistance gene, a Southern blot of PH1 callus was prepared as follows: DNA was isolated from PH1 and unselected control calli by freezing 2 g of callus in liquid nitrogen and grinding it to a fine powder which was transferred to a 30 ml Oak Ridge tube containing 6 ml extraction buffer (7M urea, 250 mM NaCl, 50 mM Tris-HCl pH 8.0, 20 mM EDTA pH 8.0, 1% sarcosine). To this was added 7 ml of phenol:chloroform 1:1, the tubes shaken and incubated at 37° C. 15 min. Samples were centrifuged at 8K for 10 min. at 4° C. The supernatant was pipetted through miracloth (Calbiochem 475855) into a disposable 15 ml tube (American Scientific Products, C3920-15A) containing 1 ml 4.4 M ammonium acetate, pH 5.2. Isopropanol, 6 ml, was added, the tubes shaken, and the samples incubated at −20° C. for 15 min. The DNA was pelleted in a Beckman TJ-6 centrifuge at the maximum speed for 5 min. at 4° C. The supernatant was discarded and the pellet was dissolved in 500 ul TE-10 (10 mM Tris-HCl pH 8.0, 10 mM EDTA pH 8.0) 15 min. at room temperature. The samples were transferred to a 1.5 ml Eppendorf tube and 100 ul 4.4 M ammonium acetate, pH 5.2 and 700 ul isopropanol were added. This was incubated at −20° C. for 15 min. and the DNA pelleted 5 min. in an Eppendorf microcentrifuge (12,000 rpm). The pellet was washed with 70% ethanol, dried, and resuspended in TE-1 (10 mM Tris-HCl pH 8.0, 1 EM EDTA).

The isolated DNA (10 ug) was digested with BamHI (NEB) and electrophoresed in a 0.8% w/v agarose gel at 15 V for 16 hrs in TAE buffer (40 mM Tris-acetate, 1 mM EDTA). The DNA within the gel was then depurinated by soaking the gel twice in 0.25 M HCl for 15 min., denatured and cleaved by soaking the gel twice in 0.5 M NaOH/1.0 M NaCl 15 min., and neutralized by soaking the gel twice in 0.5M Tris pH 7.4/3M NaCl 30 min. DNA was then blotted onto a Nytran membrane (Shleicher & Shuell) by capillary transfer overnight in 6×SSC (20×SSC, 3M NaCl, 0.3M sodium citrate pH 7.0). The membrane was baked at 80° C. for 2 hrs under vacuum. Prehybridization treatment of the membrane was done in 6×SSC, 10×Denhardt's solution, 1% SDS, 50 ug/ml denatured salmon sperm DNA using 0.25 ml prehybridization solution per $cm^2$ of membrane. Prehybridization was carried out at 42° C. overnight.

A 32P labelled probe was prepared by random primer labelling with an Oligo Labelling Kit (Pharmacia) as per the suppliers instructions with 32P-dCTP (ICN Radiochemicals). The template DNA used was the 1055 bp BamHI fragment of pHYGI1, which is the HPT coding sequence. The fragment was gel purified and cut again with PstI (NEB) before labelling.

The hybridization was performed in 50% formamide, 6×SSC, 1% SDS, 50 ug/ml denatured salmon sperm DNA (Sigma), 0.05% sodium pyrophosphate and all of the isopropanol precipitated heat denatured probe ($10^7$ CPM/50ug template). The hybridization was carried out at 42° C. overnight.

Figure 3:
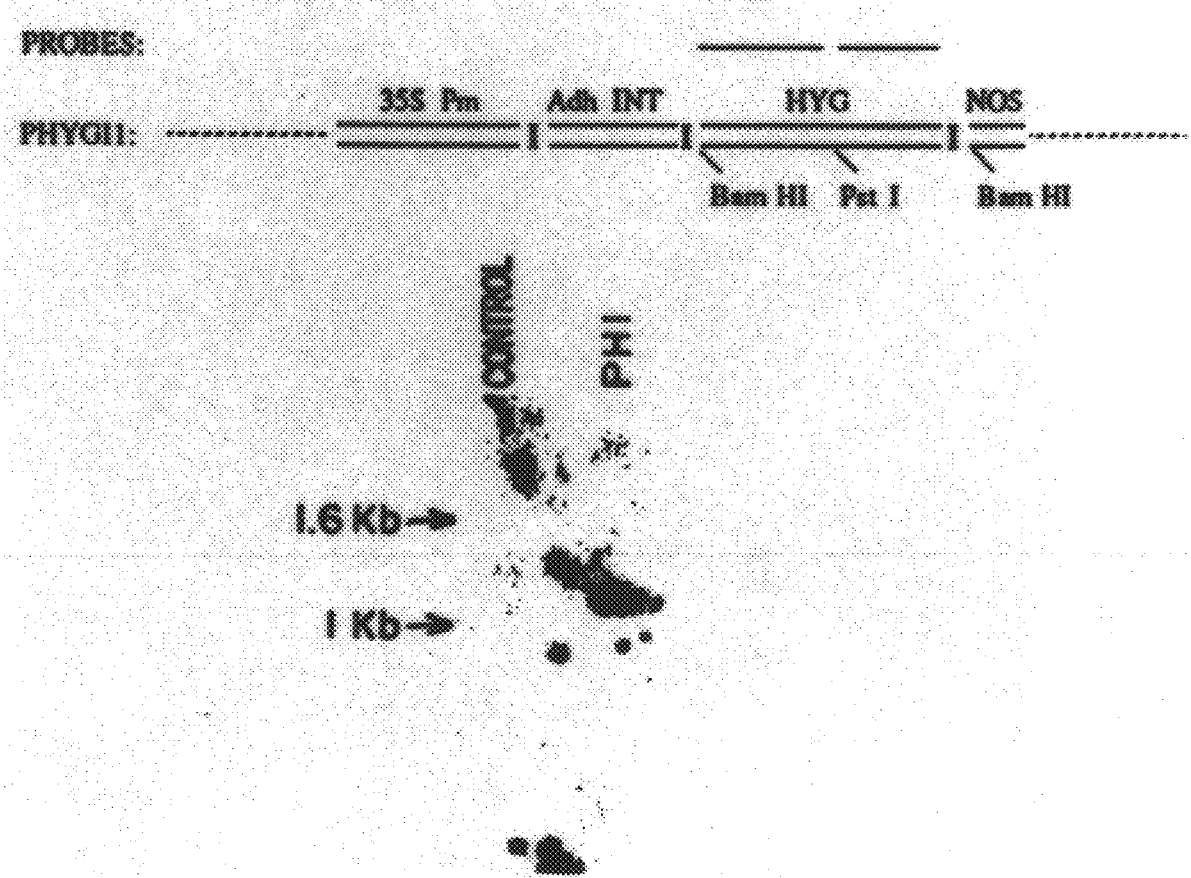
FIG. 3 is a Southern blot of DNA isolated from the PH1 callus line and an untransformed control callus line.

The membrane was washed twice in 50 ml 6×SSC, 0.1% SDS 5 min. at room temperature with shaking, then twice in 500 ml 6×SSC, 0.1% SDS 15 min. at room temperature, then twice in 500 ml 1×SSC, 1% SDS 30 min. at 42° C., and finally in 500 ml 0.1×SSC 1% SDS 60 min. at 65° C. Membranes were exposed to Kodak X-OMAT AR film in an X-OMATIC cassette with intensifying screens. As shown in FIG. 3, a band was observed for PH1 callus at the expected position of 1.05 Kb, indicating that the HPT coding sequence was present. No band was observed for control callus.

VI. Plant Regeneration and Production of Seed

PH1 callus was transferred directly from all of the concentrations of hygromycin used in the inhibition study to RM5 medium which consists of MS basal salts (Murashige et al. 1962) supplemented with thiamine HCl 0.5 mg/l, 2,4-D 0.75 mg/l, sucrose 50 g/l, asparagine 150 mg/l, and Gelrite 2.5 g/l (Kelco Inc. San Diego).

After 14 d on RM5 medium the majority of PH1 and negative control callus was transferred to R5 medium which is the same as RMT medium, except that 2,4-D is omitted. These were cultured in the dark for 7 d at 26° C. and transferred to a liaht regime of 14 hours light and 10 hours dark for 14 d at 26° C. At this point, plantlets that had formed were transferred to one quart canning jars (Ball) containing 100 ml of R5 medium. Plants were transferred from jars to vermiculite after 14 and 21 d. Plants were grown in vermiculite for 7 or 8 d before transplanting into soil and grown to maturity. A total of 65 plants were produced from PH1 and a total of 30 plants were produced from control callus.

Figure 4:
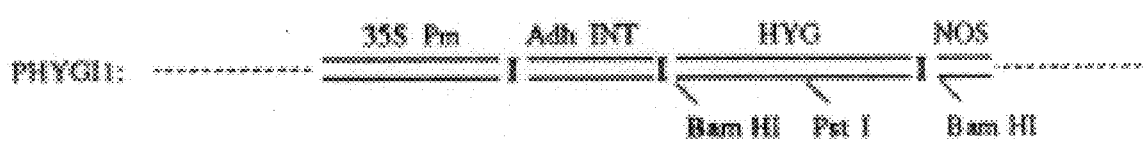
FIG. 4 is a Southern blot of leaf DNA isolated from Ro plants regenerated from PH1 and untransformed callus.
Figure 4:
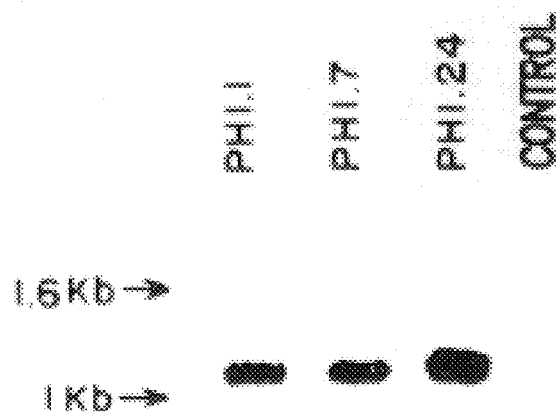

To demonstrate that the introduced DNA had been retained in the Ro tissue, a Southern blot was performed as previously described on leaf DNA from three randomly chosen Ro plants of PH1. As shown in FIG. 4, a 1.05 Kb band was observed with all three plants indicating that the HPT coding sequence was present. No band was observed for DNA from a control plant.

Controlled pollinations of mature PH1 plants were conducted by standard techniques with inbred lines A188, B73 and Oh43. Seed was harvested 45 days post-pollination and allowed to dry further 1–2 weeks. Seed set varied from 0 to 40 seeds per ear when PH1 was the female parent and from 0 to 32 seeds per ear when PH1 was the male parent.

VII. Analysis of the R1 Progeny

The presence of the hygromycin resistance trait was evaluated by a root elongation bioassay, an etiolated leaf bioassay, and by Southern blotting. Two ears each from regenerated PH1 and control plants were selected for analysis. The pollen donor was inbred line A188 for all ears.

(A) Root Elongation Bioassay

Seed was sterilized in a 1:1 dilution of commercial bleach in water plus alconox 0.1% for 20 min. in 125 ml Erlenmeyer flasks and rinsed 3 times in sterile water and imbibed overnight in sterile water containing 50 mg/ml captan by shaking at 150 rpm.

After imbibition, the solution was decanted from the flasks and the seed transferred to flow boxes (Flow Laboratories) containing 3 sheets of $H_2O$ saturated germination paper. A fourth sheet of water saturated germination paper was placed on top of the seed. Seed was allowed to germinate 4 d.

After the seed had germinated, approximately 1 cm of the primary root tip was excised from each seedling and plated on MS salts, 20 g/l sucrose, 50 mg/l hygromycin, 0.25% Gelrite, and incubated in the dark at 26° C. for 4 d.

Roots were evaluated for the presence or absence of abundant root hairs and root branches. Roots were classified as transgenic (hygromycin resistant) if they had root hairs and root branches, and untransformed (hygromycin sensitive) if they had limited numbers of branches. The results are shown in Table 1.

(B) Etiolated leaf bioassay

After the root tips were excised as described above, the seedlings of one PH1 ear and one control ear were transferred to moist vermiculite and grown in the dark for 5 d. At this point 1 mm sections were cut from the tip of the coleoptile, surface sterilized 10 seconds, and plated on MS basal salts, 20 g/l sucrose, 2.5 g/l Gelrite with either 0 (control) or 100 mg/l hygromycin and incubated in the dark at 26° C. for 18 hr. Each plate contained duplicate sections of each shoot. They were then incubated in a light regimen of 14 hours light 10 hours dark at 26° C. for 48 hr, and rated on a scale of from 0 (all brown) to 6 (all green) for the percent of green color in the leaf tissue. Shoots were classified as untransformed (hygromycin sensitive) if they had a rating of zero and classified as transformed (hygromycin resistant) if they had a rating of 3 or greater. The results are shown in Table 3.

(C) Southern Blots

Figure 5:
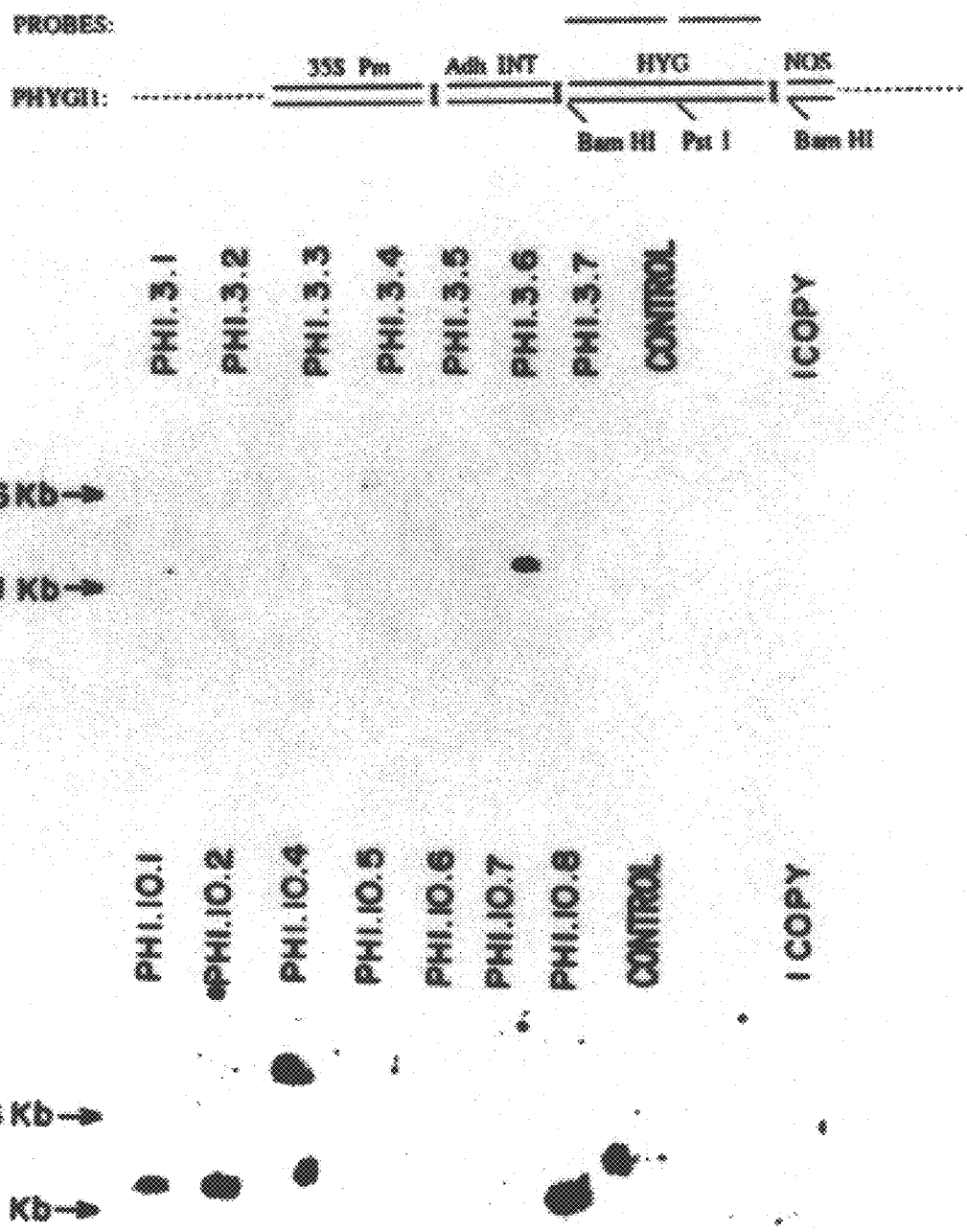
FIG. 5 is a Southern blot of leaf DNA isolated from R1 progeny of PH1 Ro plants and untransformed Ro plants.

Seedling form the bioassays were transplanted to sail and are growing to sexual maturity. DNA was isolated from 0.8 g of leaf tissue after about 3 weeks and probed with the HPT coding sequence as described previously. Plants with a 1.05 Kb band present in the Southern blot were classified as transgenic. As shown in FIG. 5, two out of seven progeny of PH1 plant 3 were transgeflic as were three out of eight progeny of PH1 plant 10. The blot results correlated precisely with data from the bioassays, confirming that the heterologous DNA was transmitted through one complete sexual life cycle. All data are summarized in Table 3.

TABLE 3

ANALYSIS OF PH1 R1 PLANTS

| PH1 PLANT | ROOT ASSAY | LEAF ASSAY | BLOT | CONT. PLANT | ROOT ASSAY | LEAF ASSAY | BLOT |
|---|---|---|---|---|---|---|---|
| 3.1 | + | ND | + | 4.1 | – | ND | ND |
| 3.2 | – | ND | – | 4.2 | – | ND | ND |
| 3.3 | – | ND | – | 4.3 | – | ND | ND |
| 3.4 | – | ND | – | 4.4 | – | ND | ND |
| 3.5 | – | ND | – | 4.5 | – | ND | ND |
| 3.6 | + | ND | + | 4.6 | – | ND | ND |
| 3.7 | – | ND | – | 4.7 | – | ND | ND |
|  |  |  |  | 2.1 | – | ND | – |
| 10.1 | + | + | + | 1.1 | – | – | – |
| 10.2 | + | + | + | 1.2 | – | – | ND |
| 10.3 | – | – | ND | 1.3 | – | – | ND |
| 10.4 | – | – | – | 1.4 | – | – | ND |
| 10.5 | – | – | – | 1.5 | – | – | ND |
| 10.6 | – | – | – | 1.6 | – | – | ND |
| 10.7 | – | – | – | 1.7 | – | – | ND |
| 10.8 | ND | + | + | 1.8 | – | – | ND |

KEY: + = transgenic; – = nontransgenic; ND = not done

EXAMPLE II

The procedure of Example I was repeated with minor modifications.

I. Plant Lines and Tissue Cultures

The embryogenic maize callus line, AB12, was used as in Example I. The line had been initiated about 18 months before the actual bombardment occurred.

II. Plasmids

The plasmids pBII221 and pHYGI1 described in Example I were used.

III. DNA delivery process

Callus was bombarded exactly as in Example I except that the DNA used in the tungsten/DNA preparations differed. All of the tubes contained 25 ul 50 mg/ml M-10 tungsten in water, 25, ul 2.5 M $CaCl_2$, and 10 ul 100 mM spermidine free base along with a total of 5 ul 1 mg/ml total plasmid content. One tube contained only plasmid pBII221; two tubes contained only plasmid pHYGI1; and one tube contained no plasmid but 5 ul TE-1 (10 mM Tris-HCl pH 8.0, 1mM EDTA pH 8.0).

The following bombardments were done:

| | |
|---|---|
| 2 × pBII221 prep | For transient expression |
| 7 × pHYGI1 prep | Potential positive treatment |
| 3 × TE prep | Negative control treatment |

After all the bombardments were performed, the callus from the pBII221 treatments was transferred plate for plate to F medium as five 50 mg pieces. After 2 d the callus was placed into GUS assay buffer as per Example I. Numbers of transiently expressing cells were counted and found to be 686 and 845 GUS positive cells, suggesting that the particle delivery process had occurred in the other bombarded plates.

27

IV. Selection of Transformed Callus

After bombardment the callus from the pHYGI1 treatments was placed onto round 1 selection plates, F medium containing 15 mg/l hygromycin, as ten 25 mg pieces per plate (different from Example I). The same was done for two of the plates bombarded with the TE preparation (selected control callus). One plate of callus bombarded with the TE preparation was placed onto F medium with no hygromycin; this callus was maintained throughout the ongoing experiment as a source of control tissue and was referred to as unselected control callus.

After 13 d the callus on round 1 selection plates was indistinguishable from unselected control callus. All of the callus was transferred from round 1 selection plates to round 2 selection plates containing 60 mg/l hygromycin. An approximate five fold expansion of the numbers of plates occurred.

The callus on round 2 selection plates had increased substantially in weight after 23 d, but at this time appeared close to dead. All of the callus was transfered from round 2 selection plates to round 3 selection plates containing 60 mg/l hygromycin. This transfer of all material from round 2 to round 3 selection differs from Example I in which only viable sectors were transferred and the round 2 plates reserved.

At 58 d post-bombardment three live sectors were observed proliferating from the surrounding dead tissue. All three lines were from pHYGI1 treatments and were designated 24C, 56A, and 55A.

After 15 d on maintainance medium, growth of the lines was observed. The line 24C grew well whereas lines 55A and 56A grew more slowly. All three lines were transferred to F medium containing 60 mg/l hygromycin. Unselected control callus from maintenance was plated to F medium having 60 mg/l hygromycin.

After 19 d on 60 mg/l hygromycin the growth of line 24C appeared to be entirely uninhibited, with the control showing approximately 80% of the weight gain of 24C. The line 56A was completely dead, and the line 55A was very close. The lines 24C and 55A were transferred again to F 60 mg/l hygromycin as was the control tissue.

After 23 d on 60 mg/l hygromycin the line 24C again appeared entirely uninhibited. The line 55A was completely dead, as was the negative control callus on its second exposure to to F 60 mg/l hygromycin.

At 88 d post-bombardment, a sector was observed proliferating among the surrounding dead tissue on the round 3 selection plates. The callus was from a plate bombarded with pHYGI1 and was designated 13E. The callus was transferred to F medium and cultured for 19 d. Portions of the callus were then transferred to (i) F media containing 15 mg/l hygromycin and (ii) F media containing 60 mg/l hygromycin. Control callus was plated on F media with 15 mg/l hygromycin. After 14 d of culture, the callus line 13E appeared uninhibited on both levels of hygromycin. The control callus appeared to have about 80% of the weight gain of 13E. The callus lines were transferred to fresh media at the same respective levels of hygromycin.

V. Confirmation of Transformed Callus

Figure 6:
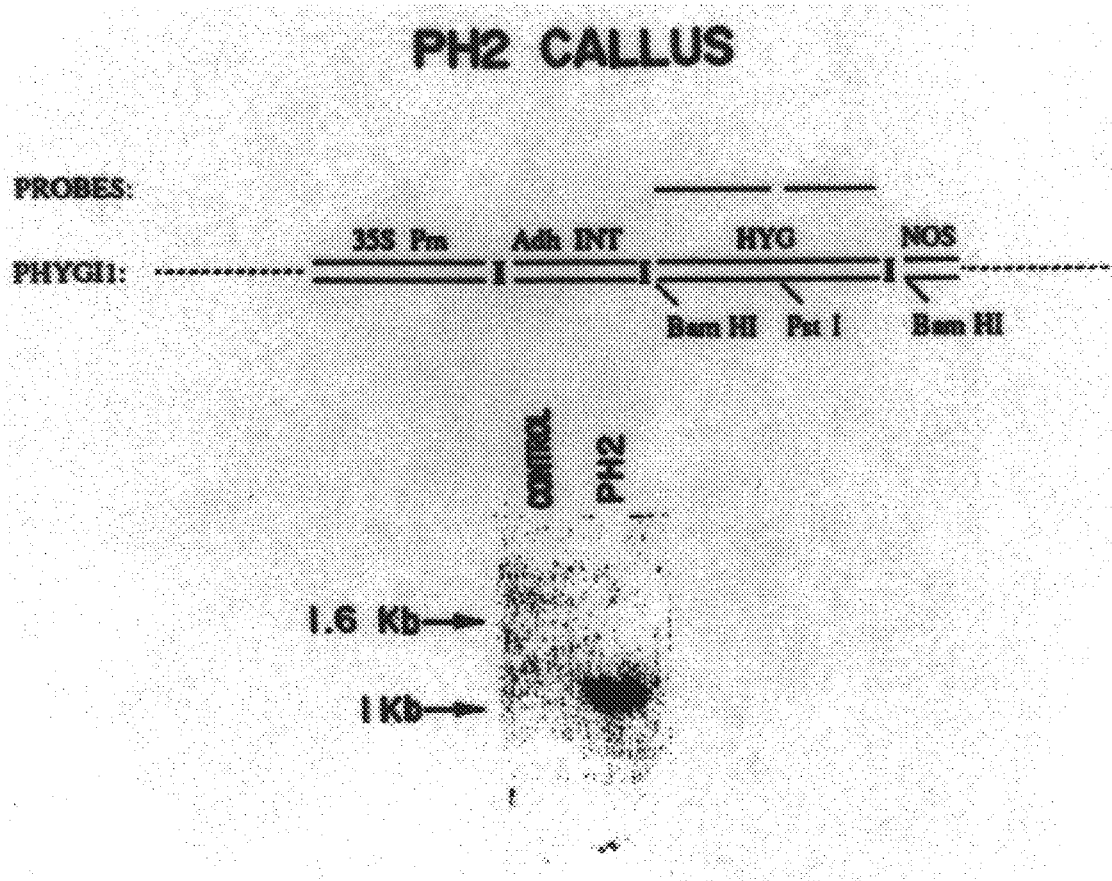
FIG. 6 is a Southern blot of DNA isolated from the PH2 callus line and an untransformed control callus line.

A Southern blot was prepared from DNA from the line 24C. As shown in FIG. 6, a band was observed for the line 24C at the expected size of 1.05 Kb showing that the line 24C contained the HPT coding sequence. No band was observed for DNA from control tissue. The name of the callus line 24C was changed to PH2.

VI. Plant Regeneration and Production of Seed

The line 24C along with unselected control callus were placed onto RM5 medium to regenerate plants as in Example I. After 16 d the callus was transferred to R5 medium as in Example I.

EXAMPLE III

The procedure of Example II was repeated exactly except that different plasmids were used.

The plasmids pBII221 and pHYGI1 described in Example I were used as well as pMS533 which is a plasmid that contains the insecticidal Bacillus thuringiensis endotoxin (BT) gene fused in frame with the neomycin phosphotransferase (NPTII) gene. 5' of the fusion gene are located segments of DNA from the CaMV 35S and nopaline synthase promoters. 3' from the fusion gene are segments of DNA derived from the tomato protease inhibitor I gene and the poly A region of the nopaline synthase gene.

Callus was bombarded exactly as in Example I except that the DNA used in the tungsten/DNA preparations differed. Two tubes contained plasmids pHYGI1 and pMS533 and one tube contained no plasmid but 5 ul TE-1 (10 mM Tris-HCl pH 8.0, 1mM EDTA pH 8.0).

The following bombardments were done:

9×pHYGI1/pMS533 Potential positive treatment

2 ×TE prep Control treatment

After bombardment the callus from the pHYGI1/pMS533 treatments was placed onto round 1 selection plates, F medium containing 15 mg/l hygromycin, as ten 25 mg pieces per plate. The same was done for one of the plates bombarded with the TE preparation (selected control callus). One plate of callus bombarded with the TE preparation was placed onto F medium with no hygromycin; this callus was maintained throughout the ongoing experiment as a source of control tissue and was referred to as unselected control callus.

After 12 d the callus on round 1 selection plates appeared to show about 90% of the weight gain of the unselected control callus. All of the callus was transferred from round 1 selection plates to round 2 selection plates containing 60 mg/l hygromycin as ten 30 mg pieces per plate.

After 22 d of selection on round 2 selection plates, the callus appeared completely uninhibited. All of the callus was transferred from round 2 selection plates to round 3 selection plates containing 60 mg/l hygromycin.

At 74 d post-bombardment a single viable sector was observed proliferating from the surrounding necrotic tissue. The callus line was from pHYGI1/pMS533 treated material and was designated 86R. The callus line 86R was transferred to F medium.

After 24 d the callus line 86R had grown substantially. Portions of the callus were then transferred to (i) F media containing 15 mg/l hygromycin and (ii) F media containing 60 mg/l hygromycin. Control callus was plated on F media with 15 mg/l hygromycin.

After 19 d of culture, the callus line 86R appeared to grow rapidly and was uninhibited on both levels of hygromycin. The control callus appeared to have only about 50% of the weight gain of 86R. The callus lines were transferred to fresh media at the same respective levels of hygromycin to further test the resistance of the callus line 86R to hygromycin.

COMPARATIVE EXAMPLE A

The basic procedures of Examples I–III have been attempted except varying the selection regime or the form of the callus. These other attempts, which are detailed in Table 4 below, were not successful. Since they were not repeated several times, it is not known whether they can be made to work. In all of the procedures, no viable sectors were observed. In the Table, "Sieved" indicates that the callus was passed through an 860 micron sieve before bombardment; the selective agent was hygromycin for each case except when pMXTI1 was the plasmid and methotrexate the selection agent.

TABLE 4

Summary of Comparative Example A

| Recip. Tissue | Plasmids | Recov. Period | Round 1 Level | Round 1 Period | Round 2 Level | Round 2 Period |
|---|---|---|---|---|---|---|
| Clumps | pCHN1-1 pBII221 | 13 | 60 | 21 | 60 | 81 |
| Clumps | pCHN1-1 pBII221 | 14 | 100 | 22 | — | — |
| Clumps | pHYGI1 pBII221 | 8 | 60 | 19 | 30 | 132 |
| Clumps | pCHN1-1 pBII221 | 0 | 30 | 22 | 60 | 109 |
| Clumps | pMTXI1 pBII221 | 8 | 3 | 103 | — | — |
| Sieved | PCHN1-1 pBII221 | 13 | — | — | — | — |

What is claimed is:

1. A process for producing a fertile transgenic *Zea mays* plant comprising the steps of (i) bombarding intact regenerable *Zea mays* cells with DNA-coated microprojectiles, wherein said DNA comprises at least a screenable marker gene; (ii) selecting a population of transformed cells expressing the selectable marker gene; and (iii) regenerating a fertile transgenic plant therefrom, wherein said DNA is expressed so as to impart glyphosate resistance to said transgenic plant and is transmitted through a normal sexual cycle of said transgenic plant to progeny plants.

2. The process of claim 1 wherein the fertile transgenic *Zea mays* plant is regenerated from transformed embryogenic tissue.

3. The process of claim 1 wherein the cells are derived from immature embryos.

4. The process of claim 1 wherein said DNA encodes an EPSP synthase.

5. The process of claim 1 further comprising obtaining transgenic glyphosate resistant progeny plants of subsequent generations from said fertile transgenic plant.

6. The process of claim 5 further comprising obtaining seed from one of said progeny plants.

7. A process for producing seed comprising:

(a) providing a fertile transgenic *Zea mays* produced by the process of claim 1, plant comprising heterologous heritable DNA that is expressed so as to impart glyphosate resistance to said transgenic *Zea mays* plant;

(b) cultivating said transgenic *Zea mays* plant;

(c) obtaining seed from said cultivated *Zea mays* plant.

8. The process of claim 7 wherein the DNA encodes an EPSP synthase.

* * * * *

UNITED STATES PATENT AND TRADEMARK OFFICE
CERTIFICATE OF CORRECTION

PATENT NO. : 6,013,863
DATED : January 11, 2000
INVENTOR(S) : Lundquist et al.

Page 1 of 2

It is certified that error appears in the above-identified patent and that said Letters Patent is hereby corrected as shown below:

Column 10,
Line 12, delete the comma and insert a prime sign, therefor.
Line 73, delete "ST.L.1" and insert -- ST.LS.1 --, therefor.

Column 11,
Line 44, delete "Nicatiana" and insert -- Nicotiana --, therefor.

Column 13-14,
In the first two rows of Table 2, delete all four occurences of "ncomycin" and insert -- neomycin --, therefor.
In the second to last row and first column of Table 2, delete "luciterase" and insert -- luciferase --, therefor.
Footnote 1, add a space between "EMBO" and "J", both occurrences.
Footnote 2, add a space between "PNAS" and "USA".
Footnote 2, underline "Nucl. Acids Res., 14,".
Footnote 3, underline "EMBO J., 3," and "Nature, 303,".
Footnote 4, underline "Nature, 310,", "ibid.," and "EMBO J., 2,".
Footnote 5, delete "Somat. Cell, Mol. Genet." and replace with -- Somat. Cell. Mol. Genet., 13, --therefore.
Footnote 6, underline "Theor, Appl. Genet., 66", Nature, 300,", "Plant Mol. Biol., 5," and "J. Mol. Appl. Genet., 2".
Footnote 7, underline "EMBO J., 4,", "Nuc. Acids Res., 14," and "EMBO J., 2,".
Footnote 8, underline "Science, 284" and "Plant Mol. Biol., 5," both occurrences.
Footnote 9, underline "Plant Mol. Biol., 2,".
Footnote 10, underline "Mol. Gen. Genet., 210,".
Footnote 11, underline "Nature, 317" and "Biotechnology, 5,".
Footnote 12, underline "EMBO J., 6,", both occurrences.
Footnote 13, underline "Biotechnology, 2,".
Footnote 14, underline "Nuc. Acids Res., 15" and "EMBO J., 6,".
Footnote 15, underline "Mol. Gen. Genet., 204,".
Footnote 16, underline "Science, 234,", "PNAS USA", and "Nucl. Acids Res., 15,".

UNITED STATES PATENT AND TRADEMARK OFFICE
CERTIFICATE OF CORRECTION

PATENT NO. : 6,013,863
DATED : January 11, 2000
INVENTOR(S) : Lundquist et al.

It is certified that error appears in the above-identified patent and that said Letters Patent is hereby corrected as shown below:

Column 29,
Line 29, delete "screenable" and insert -- selectable --, therefor.

Column 30,
Line 21, insert "plant" before -- produced --.
Line 22, insert "said" before -- plant --.

Signed and Sealed this

Twenty-third Day of October, 2001

Attest:

*Attesting Officer*

NICHOLAS P. GODICI
*Acting Director of the United States Patent and Trademark Office*